US012642616B2

(12) United States Patent
    Clark et al.

(10) Patent No.: US 12,642,616 B2
(45) Date of Patent: Jun. 2, 2026

(54) MOBILE SYSTEM FOR TRANSPORT AND STORAGE OF ROBOTIC DRIVE

(71) Applicant: Corindus, Inc., Newton, MA (US)

(72) Inventors: Andrew Clark, Arlington, MA (US);
    Allison Tse, San Leandro, CA (US);
    Eric Jones, Natick, MA (US);
    Cristopher Pavloff, San Francisco, CA
    (US); Zachary Boyer, Boxborough,
    MA (US); Vadim Kuklov, Seattle, WA
    (US); Al Costa, Pepperell, MA (US);
    Genevieve R. K. Laing, San Francisco,
    CA (US); Ryan Wood, San Anselmo,
    CA (US)

(73) Assignee: **Siemens Healthineers Endovascular
    Robotics, Inc.**, Newton, MA (US)

( * ) Notice: Subject to any disclaimer, the term of this
    patent is extended or adjusted under 35
    U.S.C. 154(b) by 280 days.

(21) Appl. No.: 18/469,870

(22) Filed: Sep. 19, 2023

(65) Prior Publication Data

US 2025/0090258 A1     Mar. 20, 2025

(51) Int. Cl.
    *A61B 50/13*      (2016.01)
    *A61B 34/30*      (2016.01)
    *A61B 50/33*      (2016.01)
    *A61B 90/50*      (2016.01)

(52) U.S. Cl.
    CPC .............. *A61B 50/13* (2016.02); *A61B 34/30*
    (2016.02); *A61B 50/33* (2016.02); *A61B 90/50*
    (2016.02); *A61B 2034/301* (2016.02)

(58) Field of Classification Search
    CPC ........ A61B 2034/301; A61B 2090/374; A61B
    2090/376; A61B 2090/3762; A61B
    2090/378; A61B 34/30; A61B 50/13;
    A61B 50/33; A61B 90/50
    See application file for complete search history.

(56) References Cited

U.S. PATENT DOCUMENTS

| | | | |
|---|---|---|---|
| 10,034,721 B1 * | 7/2018 | Timm ................... | B62B 5/0006 |
| 10,611,391 B1 | 4/2020 | Klem et al. | |
| 10,780,009 B2 | 9/2020 | Bucher et al. | |
| 2018/0333215 A1 * | 11/2018 | Timm ....................... | B62B 3/02 |
| 2020/0197111 A1 | 6/2020 | Kim et al. | |
| 2022/0125533 A1 | 4/2022 | Falb et al. | |
| 2023/0035163 A1 | 2/2023 | Klem et al. | |
| 2023/0036742 A1 | 2/2023 | McKenney et al. | |

OTHER PUBLICATIONS

Medgadget: "Hansen Medical Magellan Transport System", Aug.
29, 2014, Medgadget Editors, Cardiology, Radiology, 2pgs.

* cited by examiner

*Primary Examiner* — Scott Luan

(57)            ABSTRACT

A mobile system for a robotic drive includes a tray config-
ured to support the robotic drive, a cart configured to support
the tray in a substantially horizontal position, one or more
wheels coupled to the cart, and an assembly coupled to the
cart. The assembly is configured to allow the tray to move
from the substantially horizontal position to a second posi-
tion which is less horizontal than the substantially horizontal
position, and is configured to resist movement of the tray
from the substantially horizontal position to the second
position.

13 Claims, 24 Drawing Sheets

110

116

24

110

130b

130a

MOBILE SYSTEM FOR TRANSPORT AND STORAGE OF ROBOTIC DRIVE

FIELD

The present invention relates generally to the field of medical devices and more particularly to a system to support, transport and store a robotic drive.

BACKGROUND

Medical beds or tables are commonly used in hospitals, clinics, doctor offices or other medical environments to support a patient during evaluation and medical procedures. Various medical devices may be required to perform such evaluation/procedures. In order to maintain a stable position of these medical devices with respect to a patient, the devices may be coupled to a rail or other interface which is in turn secured to the medical bed or table. A medical bed or table will be generally referred to herein as a patient support.

During day-to-day clinical operations, it is often desirable to remove a medical device from a patient support, move the medical device to another patient support, and mount the medical device onto the other patient support for use thereon. When a medical device is not being used, it may be necessary to store the medical device in an unmounted position to avoid interference of the medical device with the performance of unrelated procedures on a patient support.

Many medical devices, such as, for example, the robotic drives described herein, are heavy and cumbersome. Accordingly, installation and removal of the devices on and from a patient support can be difficult. Once removed, the dimensions of such devices present difficulties with respect to the dimensions of hallways and doorways through which the devices are intended to travel and of spaces in which the devices are intended to be stored. The dimensions and weight-dependent inertia of the devices increase the chance of collision and damage during transport and storage, which is particularly problematic due to the sensitivity and cost of such devices and the medical errors which may result from using a damaged medical device.

Some current systems attempt to alleviate a subset of the above-noted issues by supporting a medical device using a mechanized cart. However, under mechanical drive, it is difficult to navigate the cart to a specific location with respect to the patient support and in a specific alignment to the patient support which are required for proper mounting of the medical device thereon. Even if the cart can be adequately positioned, its device-lifting mechanism may malfunction (e.g., jam) if the medical device isn't sufficiently aligned therewith. Moreover, the mechanization increases the cost, complexity, and size of the cart while decreasing its reliability.

Systems are therefore desired to facilitate installation and removal of a medical device with respect to a patient support, as well as transport and storage of such a medical device.

SUMMARY

In accordance with some embodiments, a mobile system for a robotic drive includes a tray configured to support the robotic drive, a cart to support the tray in a substantially horizontal position, one or more wheels coupled to the cart, and an assembly coupled to the cart to allow the tray to move from the substantially horizontal position to a second position which is less horizontal than the substantially horizontal position, and to resist movement of the tray from the substantially horizontal position to the second position.

In some aspects of the above embodiment, the assembly includes an axle fixedly coupled to tray and a mechanism to resist rotation of the axle during the movement of the tray from the substantially horizontal position to the second position. Also or alternatively, the embodiments may include a support arm coupled to the tray to support the tray in the substantially horizontal position. The support arm may be movably coupled to the tray during movement of the tray to the second position. A locking mechanism may releasably couple the support arm to the tray when the tray is in the substantially horizontal position.

In accordance with some embodiments, a mobile system for a robotic drive includes a tray configured to support the robotic drive, a cart comprising a support arm coupled to the tray, configured to support the tray in a substantially horizontal position and movably coupled to the tray during movement of the tray from the substantially horizontal position to a second position which is less horizontal than the substantially horizontal position, and one or more wheels coupled to the cart. A first end of the support arm may be movably coupled to the tray during movement of the tray to the second position and a second end of the support arm is rotatably coupled to the cart, and/or the cart may include a locking mechanism configured to releasably couple the support arm to the tray when the tray is in the substantially horizontal position.

According to some embodiments, operating a mobile system for a robotic drive includes placing the robotic drive into a tray of the mobile support system, the tray configured to support and/or protect the robotic drive, unlocking a locking mechanism fixedly coupling a support arm to the tray while the support arm supports the tray in a substantially horizontal position, and rotating the tray from the substantially horizontal position to a second position which is less horizontal than the substantially horizontal position while the support arm is movably coupled to the tray. Rotating the tray may include biasing a handle coupled to the tray in a substantially vertical direction.

BRIEF DESCRIPTION OF THE DRAWINGS

This application will become more fully understood from the following detailed description, taken in conjunction with the accompanying figures, wherein like reference numerals refer to like elements in which.

DETAILED DESCRIPTION

Figure 1:
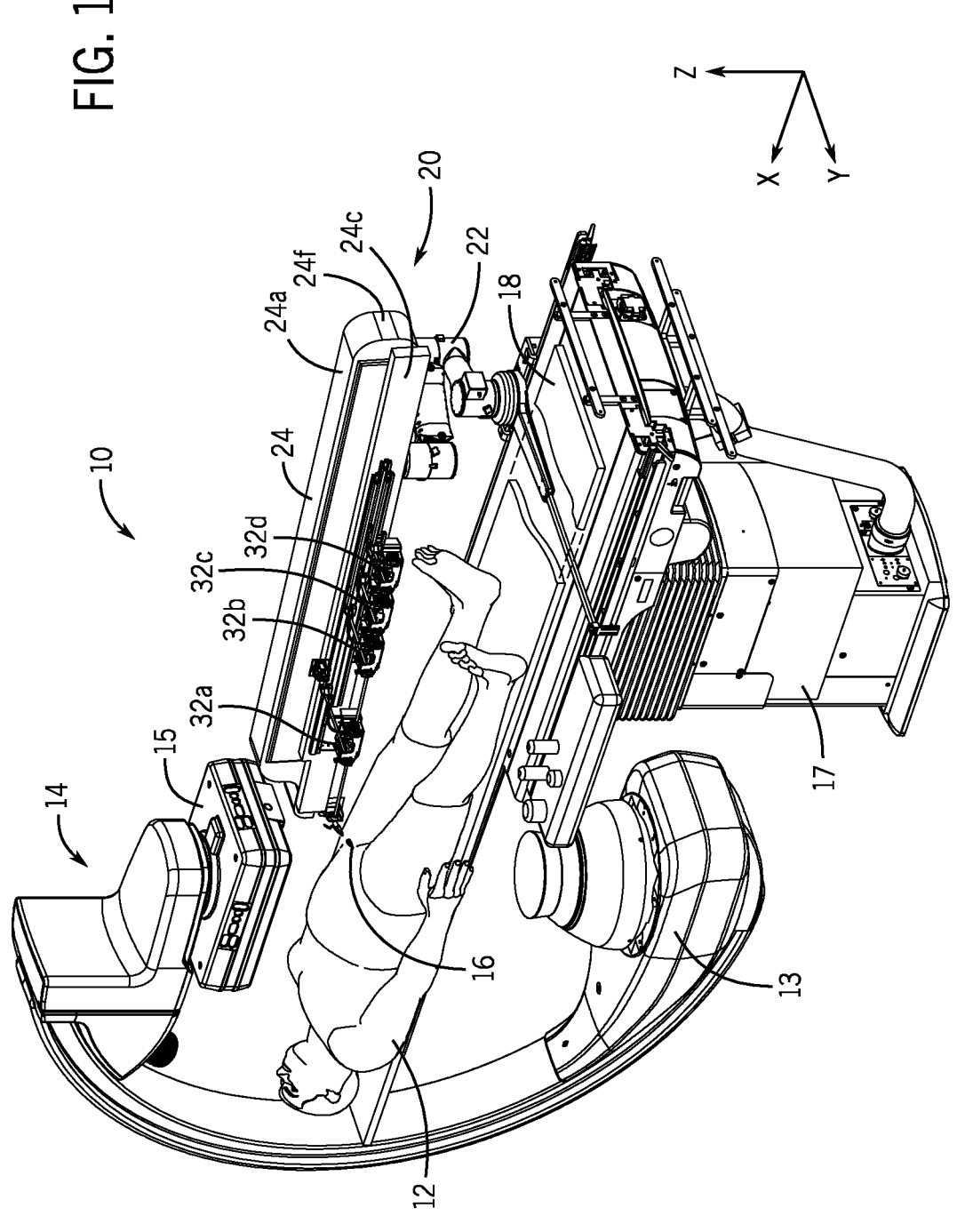
FIG. 1 is a schematic diagram of a patient support with a robotic drive mounted thereon in accordance with some embodiments.
Figure 2:
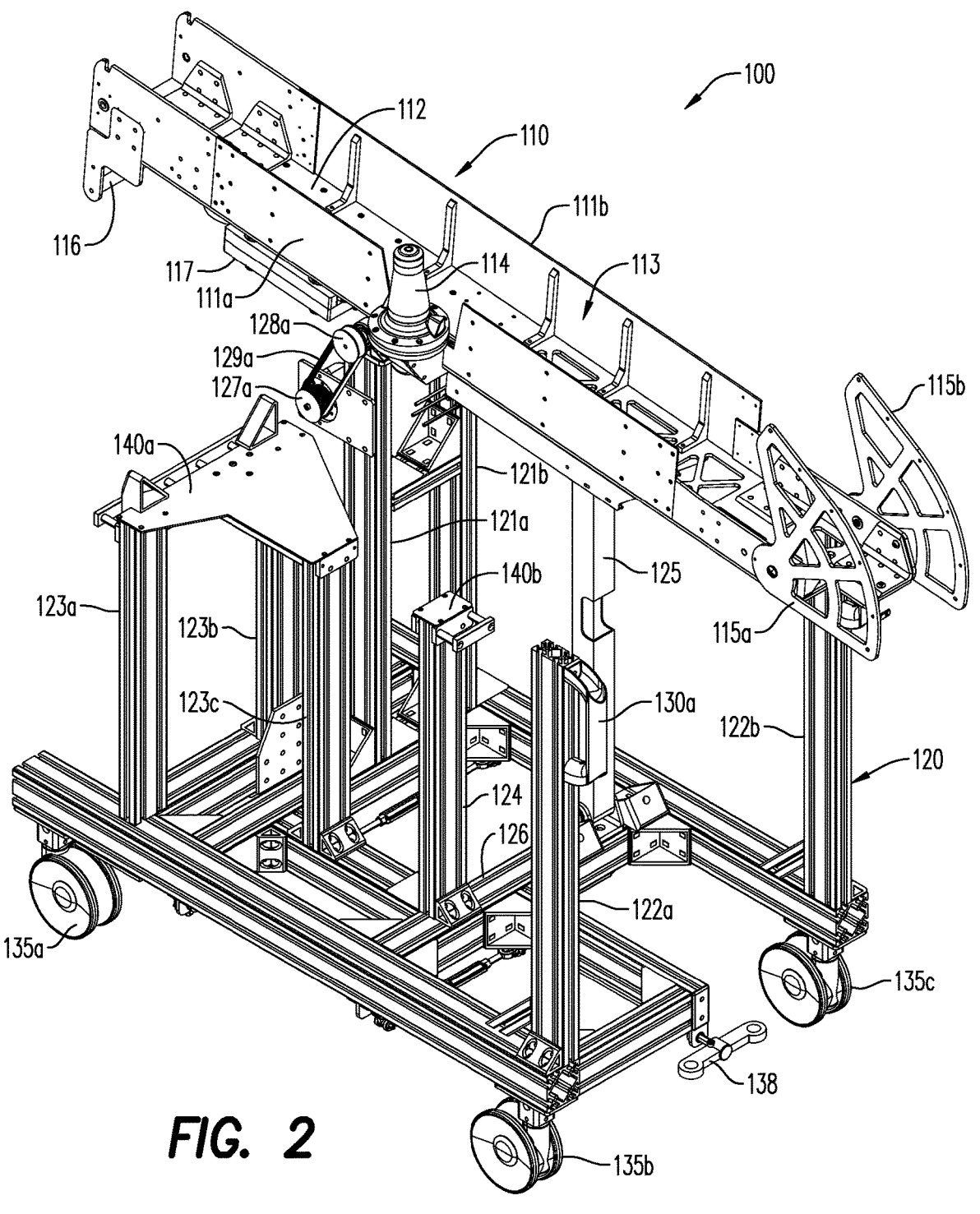
FIG. 2 is a perspective view of a mobile system including a tray in a first position in accordance with some embodiments.
Figure 3:
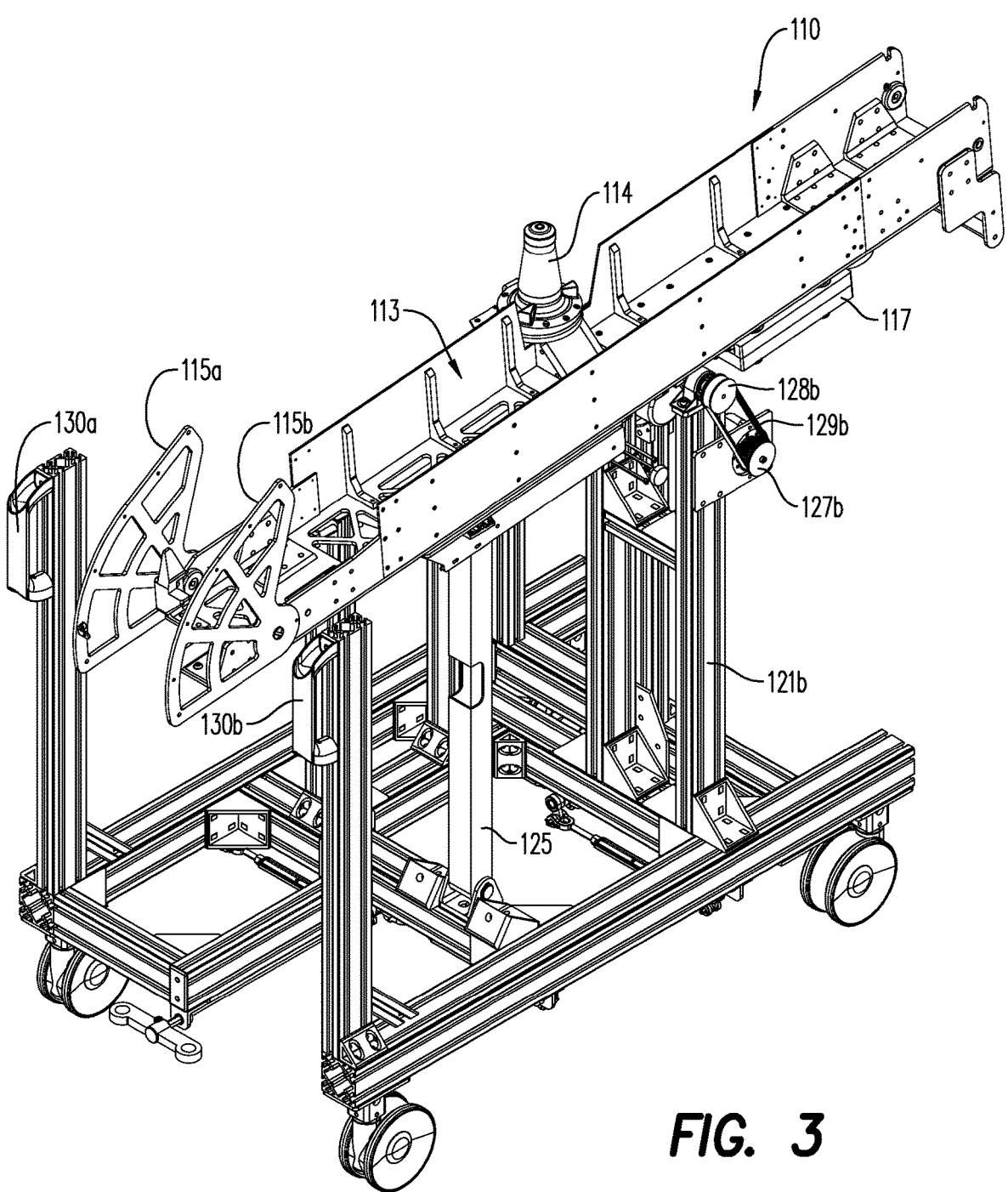
FIG. 3 is a perspective view of a mobile system including a tray in a first position in accordance with some embodiments.
Figure 4:
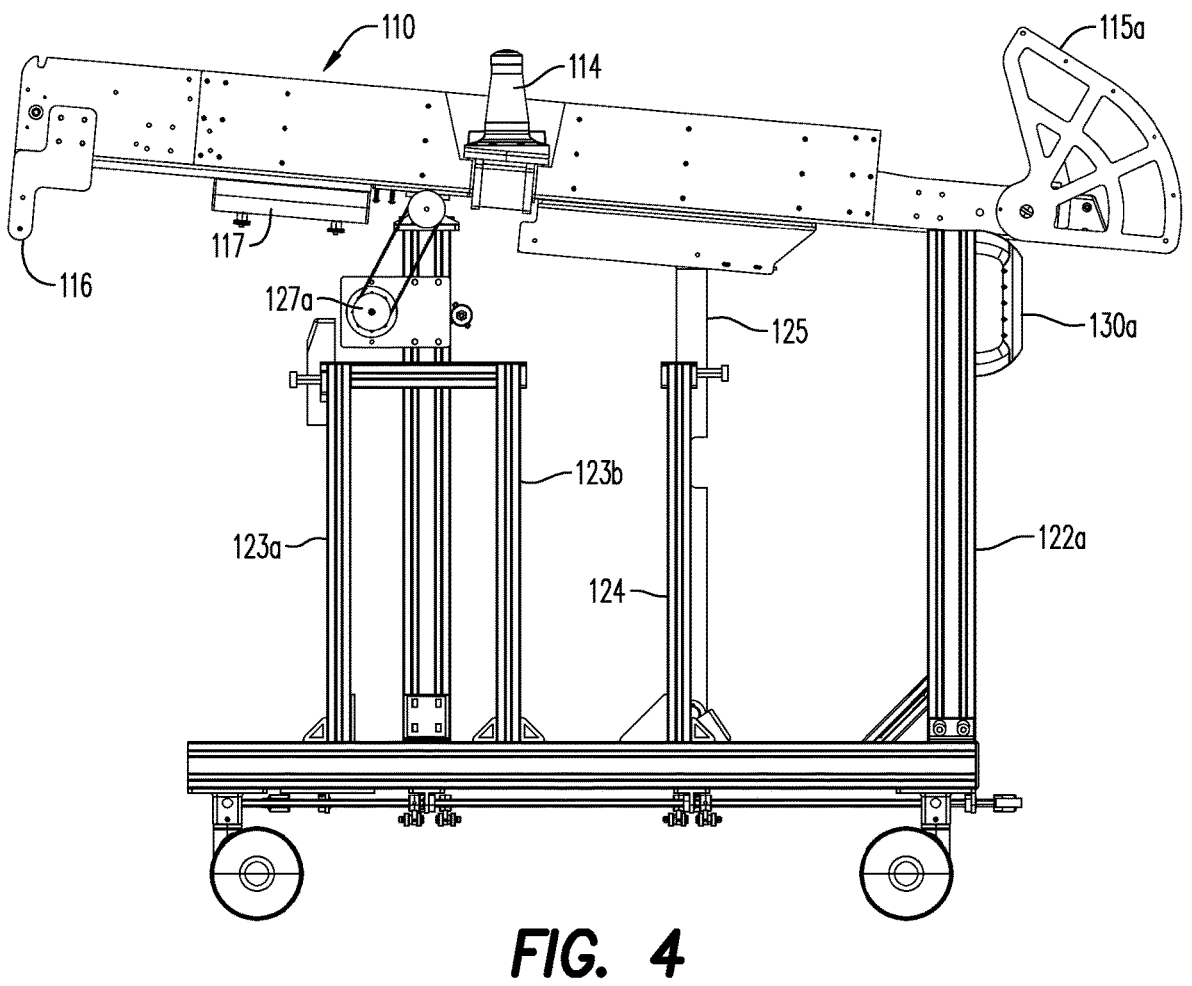
FIG. 4 is a side view of a mobile system including a tray in a first position in accordance with some embodiments.
Figure 5:
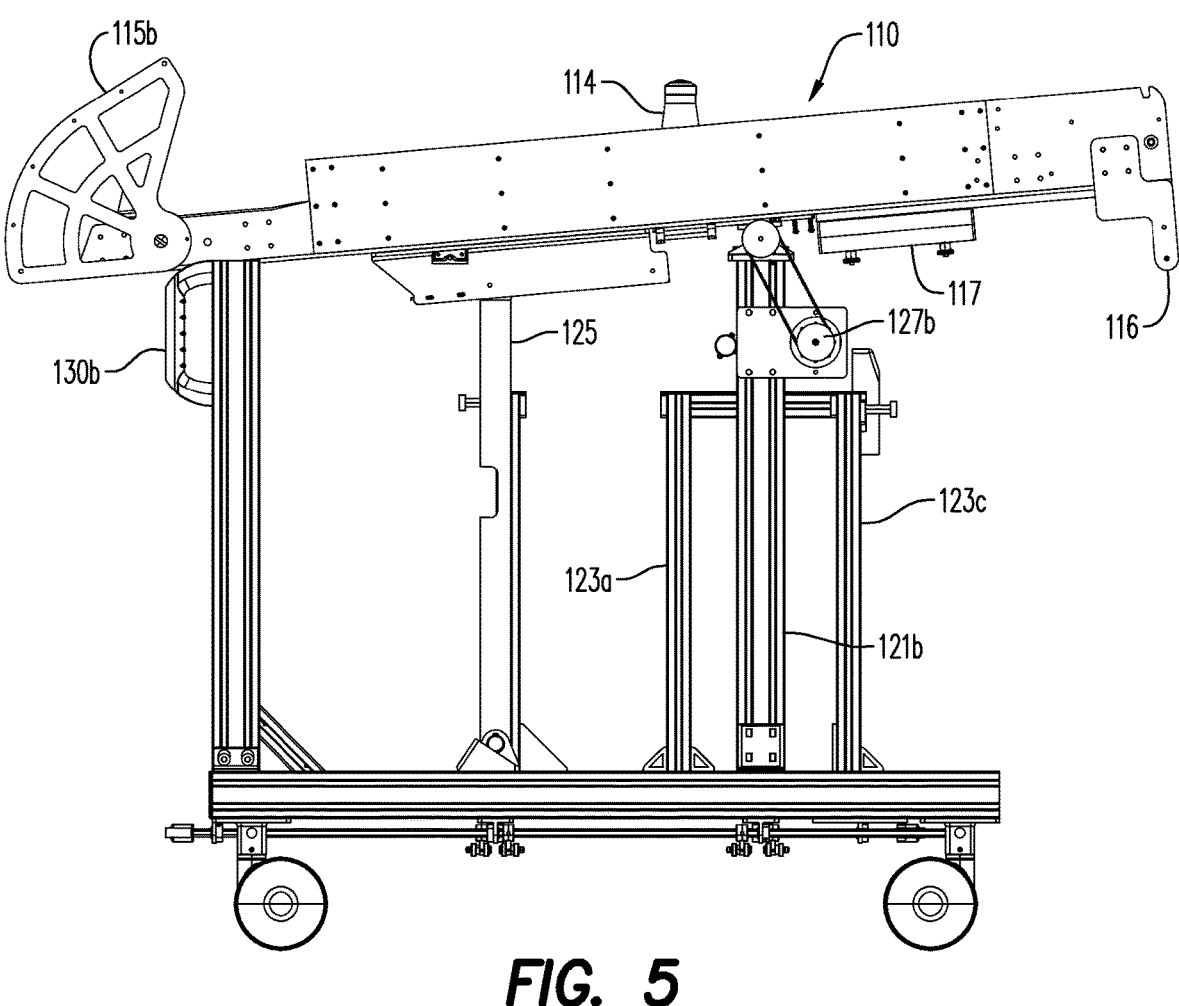
FIG. 5 is a side view of a mobile system including a tray in a first position in accordance with some embodiments.
Figure 6:
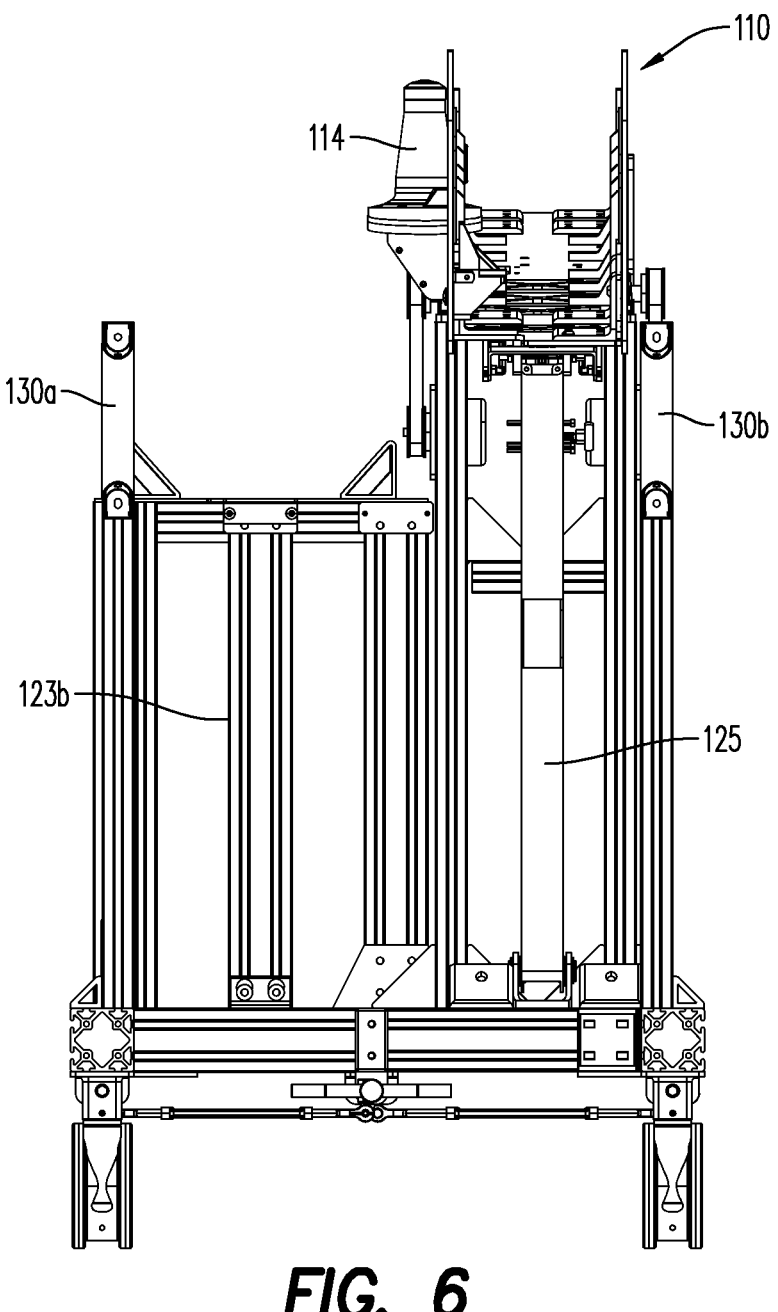
FIG. 6 is a back view of a mobile system including a tray in a first position in accordance with some embodiments.
Figure 7:
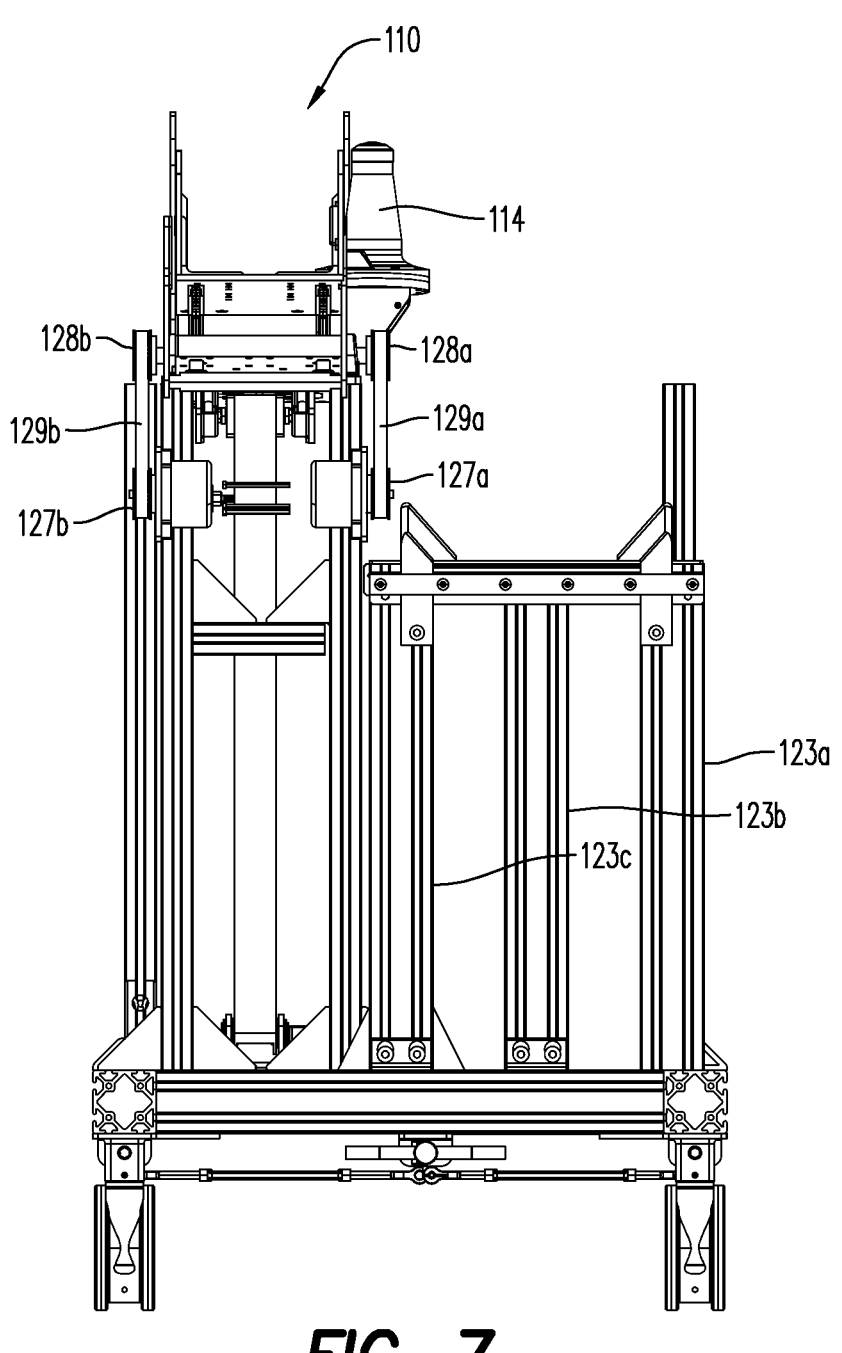
FIG. 7 is a front view of a mobile system including a tray in a first position in accordance with some embodiments.
Figure 8:
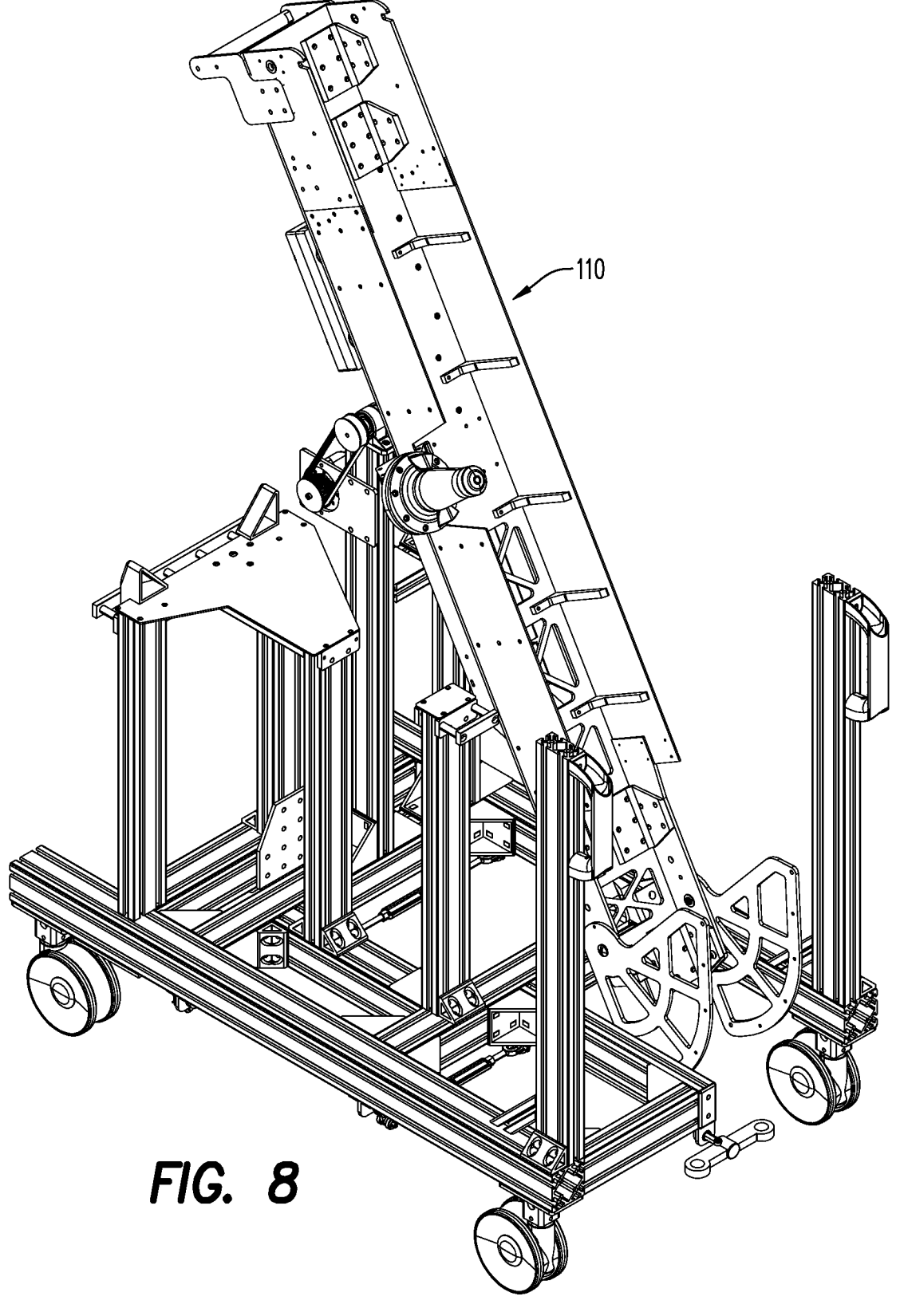
FIG. 8 is a perspective view of a mobile system including a tray in a second position in accordance with some embodiments.
Figure 9:
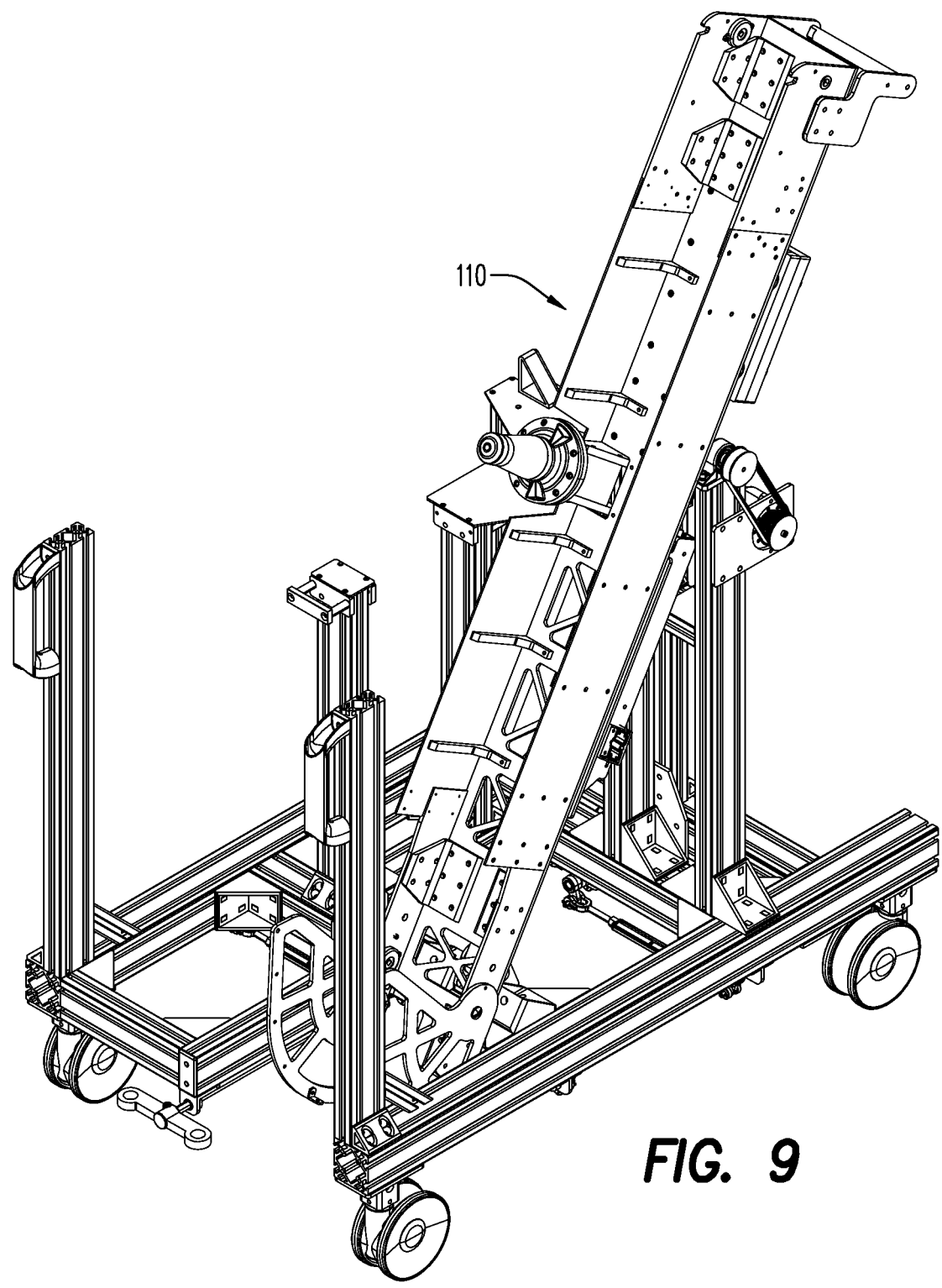
FIG. 9 is a perspective view of a mobile system including a tray in a second position in accordance with some embodiments.
Figure 10:
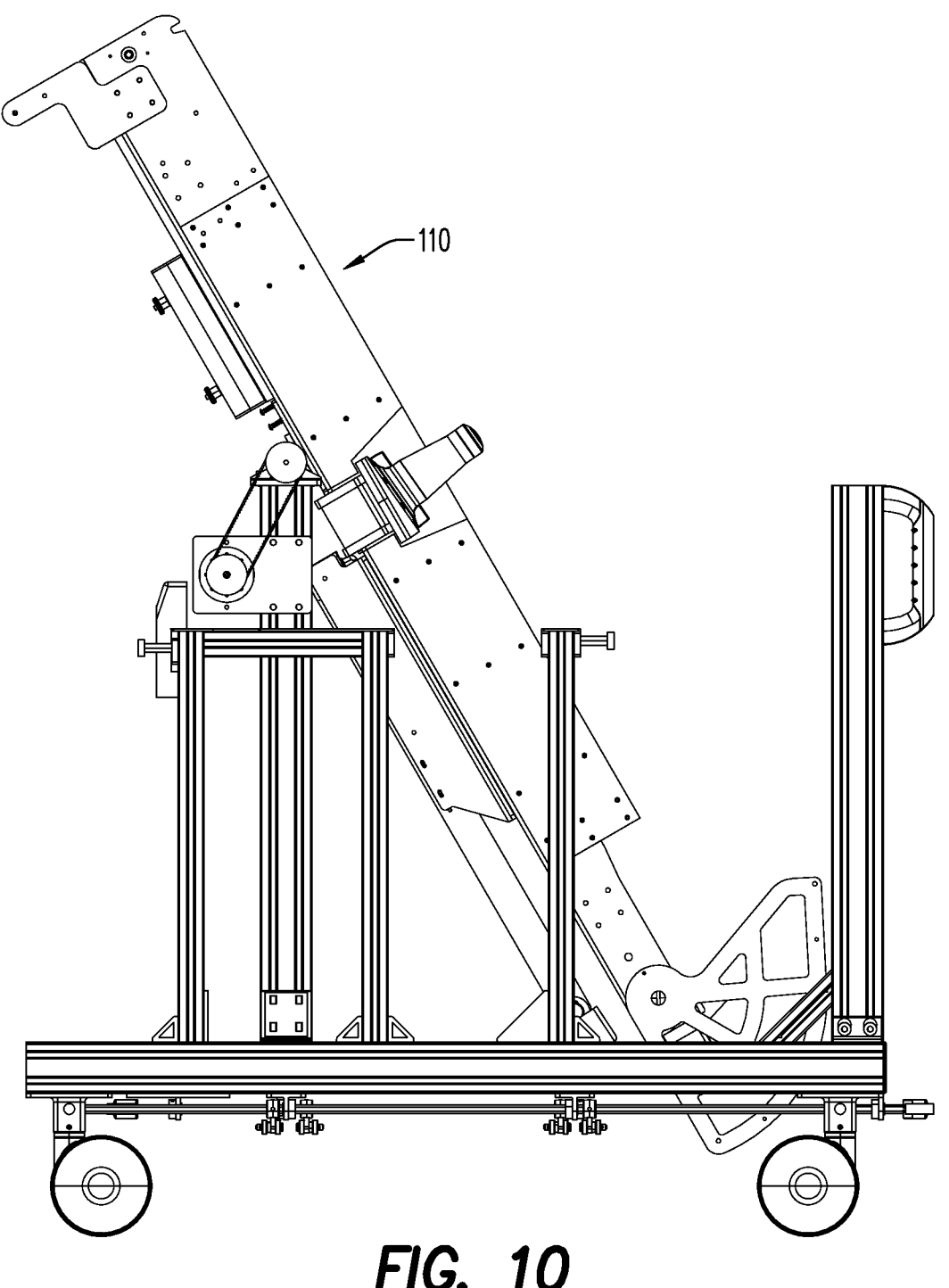
FIG. 10 is a side view of a mobile system including a tray in a second position in accordance with some embodiments.
Figure 11:
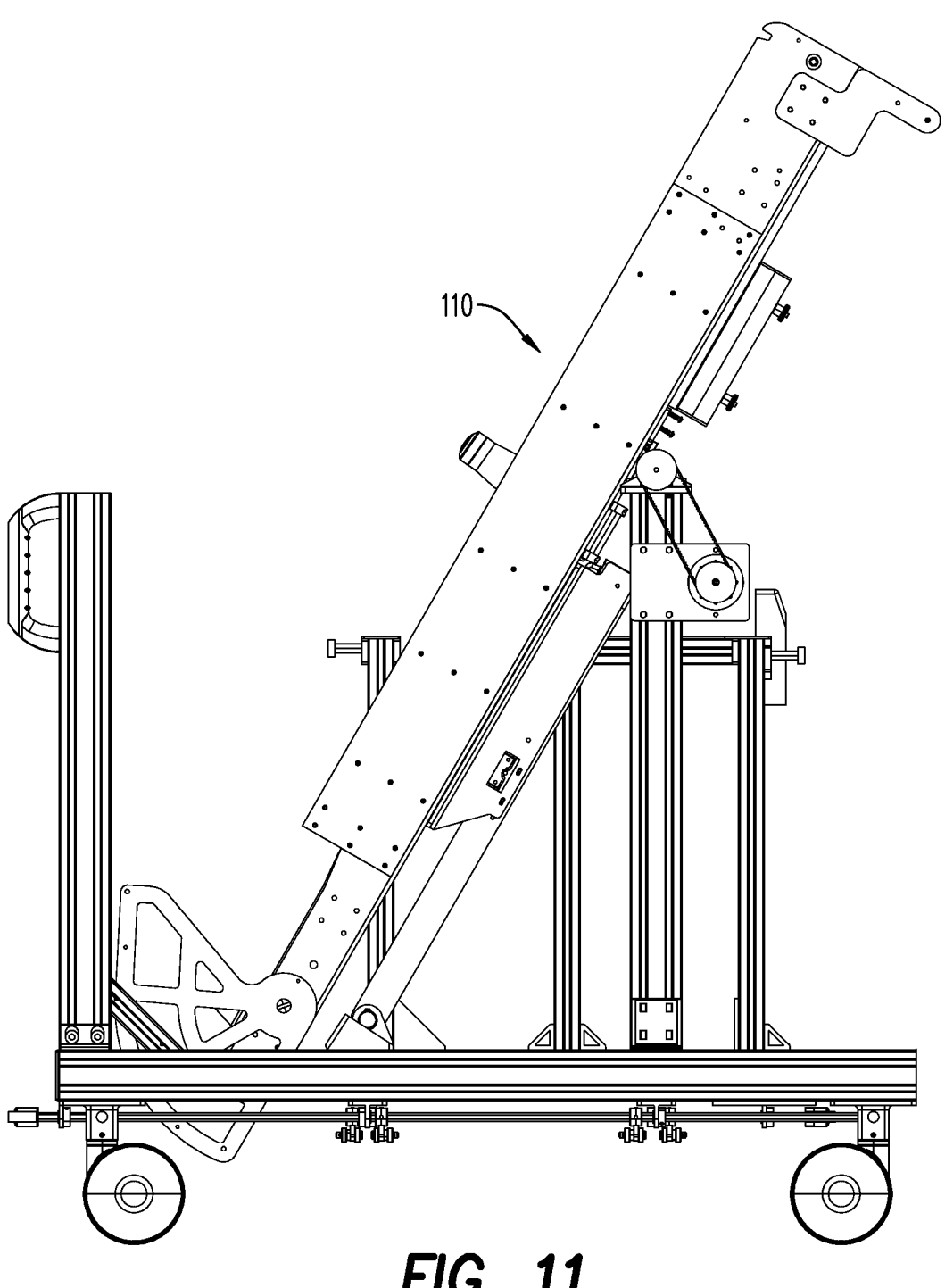
FIG. 11 is a side view of a mobile system including a tray in a second position in accordance with some embodiments.
Figure 12:
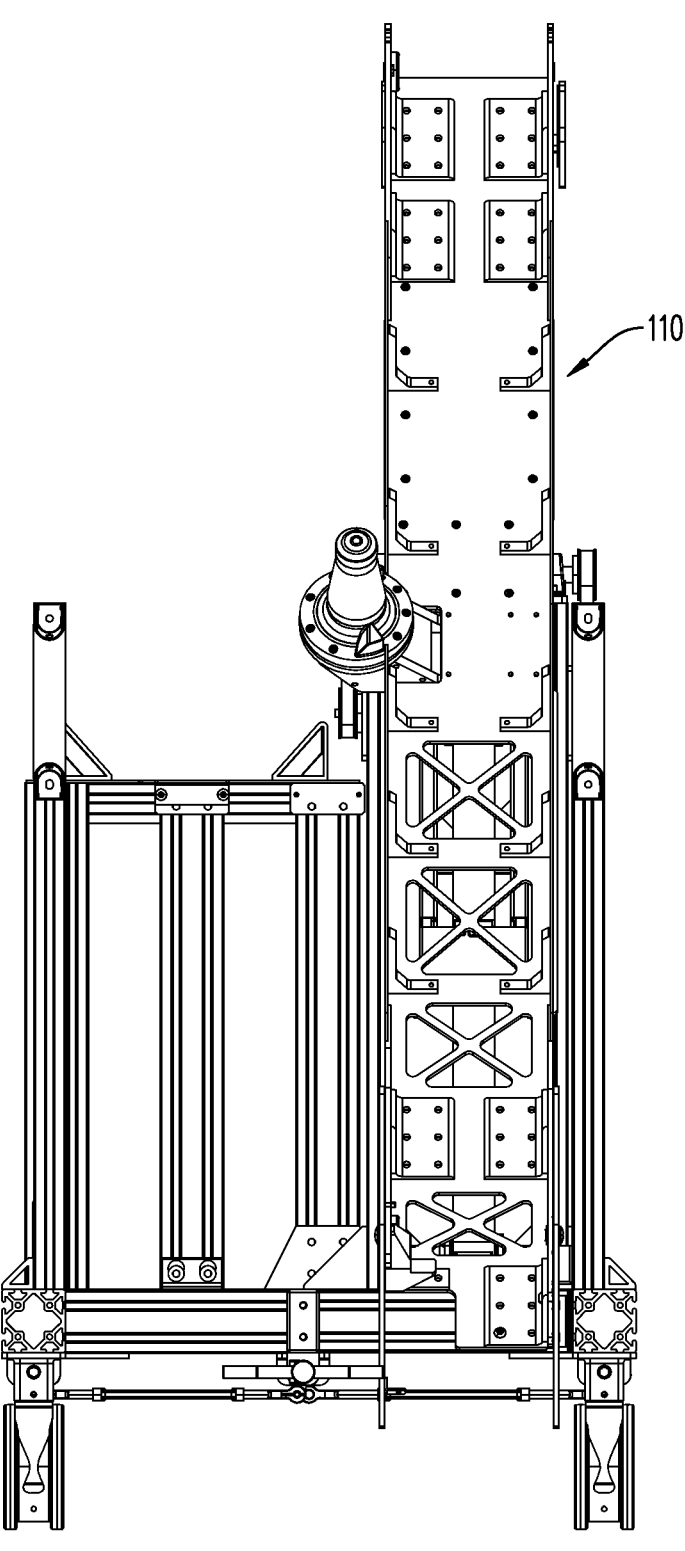
FIG. 12 is a front view of a mobile system including a tray in a second position in accordance with some embodiments.
Figure 13:
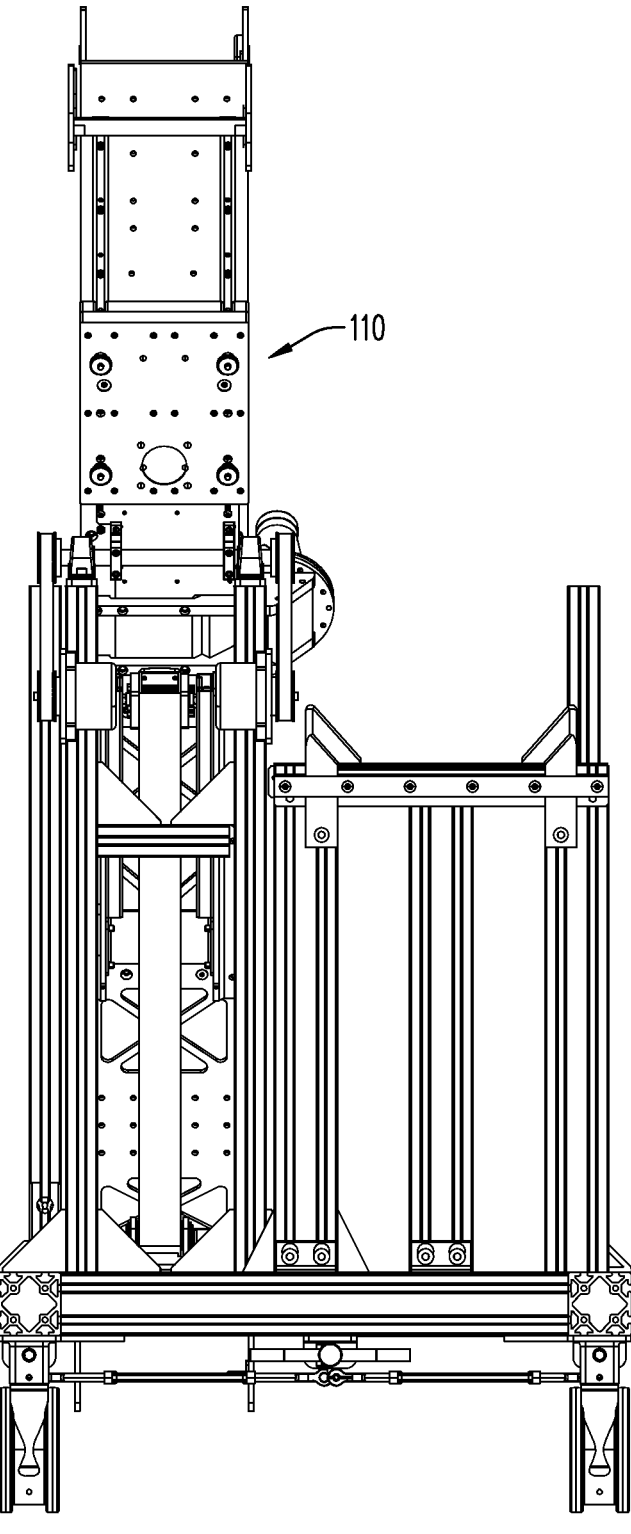
FIG. 13 is a back view of a mobile system including a tray in a second position in accordance with some embodiments.

The following description is provided to enable any person in the art to make and use the described embodiments and sets forth the various modes contemplated for carrying out the described embodiments. Various modifications, however, will remain apparent to those in the art. Independent of the grammatical term usage, individuals with male, female or other gender identities are included within the term.

Some embodiments facilitate efficient removal of a robotic drive from a patient support and mounting of a robotic drive to a patient support. Specifically, some embodiments allow quick and accurate setup of a robotic drive for clinical use by, for example, facilitating precise movement and rotation of the robotic drive with respect to the patient support, orienting the robotic drive and related components (e.g., a robotic arm) in a manner which facilitates mounting to the patient support in a desired order, and allowing the robotic drive to be removed or mounted from any side of the patient support.

Some embodiments may also allow transport of a robotic drive in a maneuverable manner which facilitates controlled movement through standard hallways and doorways. This maneuverability may be provided in part by a reduced footprint and shorter wheelbase of the mobile system, which also reduces an amount of storage area required by the mobile system and robotic drive. Some embodiments may further provide collision protection to the robotic drive via barriers integrated into a tray which supports the robotic drive during transport and storage.

As an introduction to catheter-based procedures, catheters and other elongated medical devices (EMDs) have been used in minimally-invasive medical procedures for the diagnosis and treatment of diseases of various vascular systems. These procedures include neurovascular intervention (NVI), percutaneous coronary intervention (PCI) and peripheral vascular intervention (PVI). Such procedures typically involve navigating a guidewire through the vasculature and advancing a catheter via the guidewire to deliver therapy.

A catheter-based procedure typically begins by inserting an introducer sheath to gain access into the appropriate vessel, such as an artery or vein. Through the introducer sheath, a sheath or guide catheter is then advanced over a diagnostic guidewire to a primary location such as an internal carotid artery for NVI, a coronary ostium for PCI, or a superficial femoral artery for PVI. A guidewire suitable for the vasculature is then navigated through the sheath or guide catheter to a target location in the vasculature. In certain situations, such as in tortuous anatomy, a support catheter or microcatheter is inserted over the guidewire to assist in navigating the guidewire. The physician or operator may use an imaging system (e.g., a fluoroscope) to obtain a cine with a contrast injection and select a fixed frame thereof for use as a roadmap to navigate the guidewire or catheter to the target location. Contrast-enhanced images are also obtained while the physician delivers the guidewire or catheter so that the physician can verify that the device is moving along the correct path to the target location.

Robotic drive-enabled systems may be used to aid a physician in performing catheter-based procedures. FIG. 1 is a perspective view of robotic drive-enabled catheter-based procedure system 10 in accordance with some embodiments.

Catheter-based procedure system 10 may perform catheter-based procedures such as diagnostic procedures during which one or more catheters or EMDs are used to aid in the diagnosis of a patient's disease. For example, a contrast media may be injected into one or more arteries through a catheter and an image of the patient's vasculature may be acquired soon thereafter. Catheter-based procedures may also include catheter-based therapeutic procedures (e.g., angioplasty, stent placement, treatment of peripheral vascular disease, clot removal, arterial venous malformation therapy, treatment of aneurysm, etc.) during which a catheter (or other EvD) is used to treat a disease.

Catheter-based procedure system 10 can perform any number of catheter-based medical procedures incorporating minor adjustments to accommodate the specific percutaneous intervention devices (e.g., type of guidewire, type of catheter) to be used in the procedure. The procedures may be enhanced through the use of adjunct devices such as, for example, intravascular ultrasound (IVUS), optical coherence tomography (OCT), and fractional flow reserve (FFR).

As shown, patient 12 is supported on patient table 18. In some embodiments, patient table 18 is operably supported by pedestal 17, which is secured to the floor and/or earth. Patient table 18 is able to move with multiple degrees of freedom, for example, roll, pitch, and yaw, relative to pedestal 17.

Catheter-based procedure system 10 includes, among other elements, bedside unit 20 and a control station (not shown). Bedside unit 20 includes positioning system 22 and robotic drive 24. Positioning system 22 is used to support and position robotic drive 24 with respect to patient 18. Positioning system 22 may be, for example, a robotic arm, an articulated arm, or a holder. Bedside unit 20 may also include various controls and displays for control thereof. In one example, the controls and displays are located on a housing of robotic drive 24.

One end of positioning system 22 may be attached to patient table 18 via a clamping mechanism. In one example, positioning system 22 clamps directly to table 18 and, in another system, positioning system 22 clamps to a rail mounted on table 18. The other end of positioning system 22 is attached to robotic drive 24.

Positioning system 22 and robotic drive 24 may be moved out of the way or removed from table 18 altogether to allow for patient 12 to be placed on patient table 18. Once patient 12 is placed on table 18, positioning system 22 may be controlled to properly position robotic drive 24 relative to the patient 12 for an upcoming procedure.

Robotic drive 24 may be equipped with the appropriate EMDs and accessories (e.g., guidewires, various types of catheters including but not limited to balloon catheters, stent delivery systems, stent retrievers, embolization coils, liquid embolics, aspiration pumps, device to deliver contrast media, medicine, hemostasis valve adapters, syringes, stopcocks, inflation device) to allow an operator to perform a catheter-based medical procedure by operating various controls such as the controls and inputs located at the control station.

Robotic drive 24 includes various mechanisms to cause movement (e.g., axial and rotational movement) of EMDs. In some embodiments, robotic drive 24 includes a plurality of device modules 32a-d mounted to a rail or linear member. Each of the device modules 32a-d may be used to advance, retract, or rotate an EMD such as a catheter or guidewire. For example, robotic drive 24 may be used to automatically feed a guidewire into a diagnostic catheter and into a guide catheter in an artery of patient 12 at insertion point 16 via, for example, an introducer sheath. Each device module 32a-d includes a drive module and cassette removably attached to the drive module. Each drive module is movable along the longitudinal axis of robotic drive 24. While FIG. 1 illustrates four device modules it is contemplated that robotic drive 24 may include one or more device modules.

Bedside unit 20 is in communication with a control station (not shown) to allow signals generated by the user inputs of the control station to be transmitted wirelessly or via hardwire to bedside unit 20 to control various functions of bedside unit 20. The control station may include a control computing system or be coupled to bedside unit 20 through the control computing system. Bedside unit 20 may also provide feedback signals (e.g., loads, speeds, operating conditions, warning signals, error codes, etc.) to the control station, control computing system, or both.

The control station or other similar control system may be located in the same room as or an adjacent room to patient 12 and bedside unit 20. A control station (and a control computing system) may be located at a remote site (e.g., a different building in the same city, or different cities) and control bedside unit 20 over the Internet.

Catheter-based procedure system 10 also includes imaging system 14. Imaging system 14 may comprise a fluoroscopy system including a C-arm having X-ray source 13 and detector 15, also known as an image intensifier. Imaging system 14 may be any medical imaging system that may be used in conjunction with a catheter based medical procedure (e.g., non-digital X-ray, digital X-ray, CT, MRI, ultrasound). The C-arm of imaging system 14 allows imaging system 14 to rotate partially or completely around patient 12 in order to obtain images at different angular positions relative to patient 12 (e.g., sagittal views, caudal views, anterior-posterior views).

Imaging system 14 may be configured to acquire X-ray images of an appropriate area of patient 12 during a procedure. For example, imaging system 14 may be configured to acquire one or more X-ray images of the head to diagnose a neurovascular condition. Imaging system 14 may also be configured to acquire one or more X-ray images during a catheter-based procedure (e.g., real time images) which are displayed to assist the operator in properly positioning a guidewire, guide catheter, microcatheter, stent retriever, coil, stent, balloon, etc. during the procedure.

The rectangular coordinate system of FIG. 1 includes X, Y, and Z axes. The positive X axis is oriented in a longitudinal (axial) distal direction along a longitudinal axis of robotic drive 24. The Y and Z axes are in a plane transverse to the X axis, with the positive Z axis oriented in the opposite direction of gravity, and the Y axis defined according to the right-hand rule.

FIGS. 2-13 are views of mobile system 100 in accordance with some embodiments. Mobile system 100 is configured to receive, transport and store a robotic drive. According to some embodiments, mobile system is configured to receive, transport and store a robotic drive and a positioning system such as a robotic arm 23.

Mobile system 100 includes tray 110 configured to support a robotic drive. FIGS. 2-7 show tray 110 supported by cart 120 in a substantially horizontal position. Tray 110 may be positioned in the substantially horizontal position when moving a robotic drive from a patient support to tray 110 or when removing a robotic drive from tray 110 to install the robotic drive on a patient support.

The various elements of tray 110 may be fabricated from plastic, metal and/or any other suitable material. Tray 110 includes side wall 111a, side wall 111b and base 112 defining internal volume 113. As shown, various support brackets or members may be attached to side wall 111a, side wall 111b and base 112 to provide rigidity to tray 110 while allowing side wall 111a, side wall 111b and base 112 to remain relatively light and thin.

According to some embodiments, one or both of side wall 111a and side wall 111b may be removed from tray 110 and replaced thereafter. Alternatively, one or both of side wall 111a and side wall 111b are movable with respect to base 112. For example, one or both of side wall 111a and side wall 111b may be rotated downward (i.e., in the negative Z direction) around its edge interfacing with base 112. Such removal/movement may facilitate placement of a robotic drive into tray 110 or removal of a robotic drive therefrom, particularly in a case that one side of tray 110 (e.g., side wall 111b) is located adjacent to a patient support.

Shields 115a and 115b are attached to tray 110 and may protect an end of a robotic drive placed in tray 110, as will be described below. According to some embodiments, shields 115a and 115b may rotate around their respective points of connection to tray 110. Such rotation may also facilitate placement of a robotic drive into tray 110 or removal of a robotic drive therefrom.

Tray 110 includes projection interface 114 which may be accepted into a corresponding structure of a robotic drive during placement of the robotic drive into internal volume 113 of tray 110. According to some embodiments, the robotic drive is supported completely by projection interface 114 and does not touch other surfaces of tray 110 during operation. Examples of projection interface 114 and its interaction with the robotic drive are described in detail in U.S. patent application Ser. No. 17/813,138 (U.S. Patent Application Publication No. 2023/0036742), which is incorporated by reference herein. The internal dimensions and interfacing elements of tray 110 may be designed to suitably accept and secure any type of robotic drive or robotic drives which mobile system 100 is intended to support. According to one non-exhaustive embodiment, tray 110 is approximately 1940 mm in length and 325 mm in width and is intended to support and/or protect a robotic drive which is approximately 2000 in length and 312 in width.

Handle 116 is attached to tray 110. As will be described below, an operator may use handle to bias tray 110 from the substantially horizontal position depicted in FIGS. 2-7 to a less horizontal position, and to bias tray 110 from the less horizontal position back to the depicted substantially horizontal position.

Cart 120 includes columns 121a and 121b to support tray 110. As will be described below, intermediate elements may exist between columns 121a and 121b and support tray 110. In this regard, "support" as used herein does not necessarily indicate that the supporting object is in direct physical contact with the supported object. The columns (and horizontal members attached to the columns) of cart 120 may be aluminum or any other suitable material. The columns and/or members may be hollow and constructed with rigidity-providing features to provide strength and reduced weight.

Handles 130a and 130b are attached to columns 122a and 122b, respectively. An operator may use handles 130a and 130b to push, pull and otherwise maneuver cart 120. Handles 130a and 130b may be used to maneuver cart 120 whether or not tray 110 supports a robotic drive, and whether or not tray 110 is in the substantially horizontal position or a less horizontal position.

Columns 123a, 123b and 123c of cart 120 support platform 140a, and columns 124 supports platform 140b. Platform 140a and platform 140b may together support a positioning system for a robotic drive such as positioning system 22. Platform 140a and platform 140b may be configured in any manner suitable to support and removably retain a robotic drive positioning system. Accordingly, mobile system 100 may be used in some embodiments to simultaneously support, transport and store both a robotic drive and a positioning system for the robotic drive.

Support arm 125 of cart 120 is configured to support tray 110 in the depicted substantially horizontal position. Moreover, as will be described in detail below with respect to FIGS. 19-22, support arm 125 is movably coupled to tray 110 during movement of tray 110 from the substantially horizontal position to a second position which is less horizontal than the substantially horizontal position. During such movement, support arm 125 rotates around the end of support arm 125 which is coupled to horizontal member 126.

FIGS. 8-13 show tray 110 supported by cart 120 in a position which is less horizontal and more vertical than the substantially horizontal position of FIGS. 2-7. Tray 110 may be rotated to the position shown in FIGS. 8-13 when the robotic device is not in use and is being stored.

The angle of tray 110 in the FIGS. 8-13 position may be configured to result in a suitable length and height of system 100 during transport. The angle may be increased (decreased) by raising (lowering) the point at which tray 110 pivots on cart 120. Generally, increasing the tray angle results in a shorter cart length. A shorter cart length improves maneuverability in a small space, such as a procedure room. In some embodiments, a tray angle of 65 degrees results in a total cart length of 42 in.

In a case that a weight of the robotic drive is unevenly distributed toward the end of tray 110 at which shields 115a and 115b are located, the rotation of tray 110 between the FIGS. 2-7 and FIGS. 8-13 positions may be assisted by counterweights 117 mounted to the bottom of tray 110. Regardless of the presence of counterweights 117, high speeds may be experienced during this rotation, which may pose a collision risk to nearby users or equipment or an impact risk to a robotic drive supported by tray 110. Some embodiments include an additional shock absorber at the end of rotation in either direction to prevent the tray 110 from slamming at either end.

Columns 121a and 121b also support a mechanism consisting of dampers 127a and 127b, pulleys 128a and 128b, and belts 129a and 129b. Pulleys 128a and 128b are coupled to and coaxial with an axle to which tray 110 is also coupled. The axle and the mechanism may be considered an assembly configured to allow the tray to move from the substantially horizontal position to a less horizontal position. The assembly may also operate to resist this movement. In particular, the mechanism consisting of dampers 127a and 127b, pulleys 128a and 128b, and belts 129a and 129b may be configured to resist rotation of the axle by transferring torque to the axle so as to control the speed at which tray 110 rotates between the substantially horizontal and the less horizontal positions.

According to some embodiments, dampers 127a and 127b are one-way fluid-filled dampers which resist rotation of the axle in respective opposite directions. For example, during rotation of tray 110 from the substantially horizontal position to the less horizontal position, damper 127a may, via belt 129a and pulley 128a, apply torque to the axle in a direction opposite to the rotation of the axle, while damper 127b may apply no significant torque to the axle. During of rotation of tray 110 from the less horizontal position to the substantially horizontal position, damper 127b may apply torque to the axle, via belt 129b and pulley 128b, in a direction opposite to the rotation of the axle, while damper 127a may apply no significant torque thereto.

The torque needed to adequately control rotation of tray 110 from the substantially horizontal position to the less horizontal position may be greater than the torque needed to adequately control rotation of tray 110 from the less horizontal position to the substantially horizontal position. Accordingly, in the above example, damper 127a may be tuned to apply more torque than damper 127b. In some embodiments, opposing torque is only applied to the axle by a damper during rotation of tray 110 from the substantially horizontal position to the less horizontal position and rotation of the axle is not substantially resisted during the movement of the tray from the less horizontal position to the substantially horizontal position.

Casters 135a-135d are attached to cart 120 and each include two wheels. According to some embodiments, casters 135a-135d are controlled by a mechanical system similar to those used in hospital stretchers. Using activation pedal 138, each of casters 135a-135d can be allowed to swivel and roll, allowing maximum maneuverability of system 100. In another mode selectable by activation pedal 138, two or four casters can be locked in a straight non-swiveling orientation to ease steering and increase control (e.g., when moving system 100 through hallways). A third mode selectable by activation pedal 138 locks rotation and swiveling of all casters 135a-135d, thereby parking mobile system 100 in place.

Figure 14A:
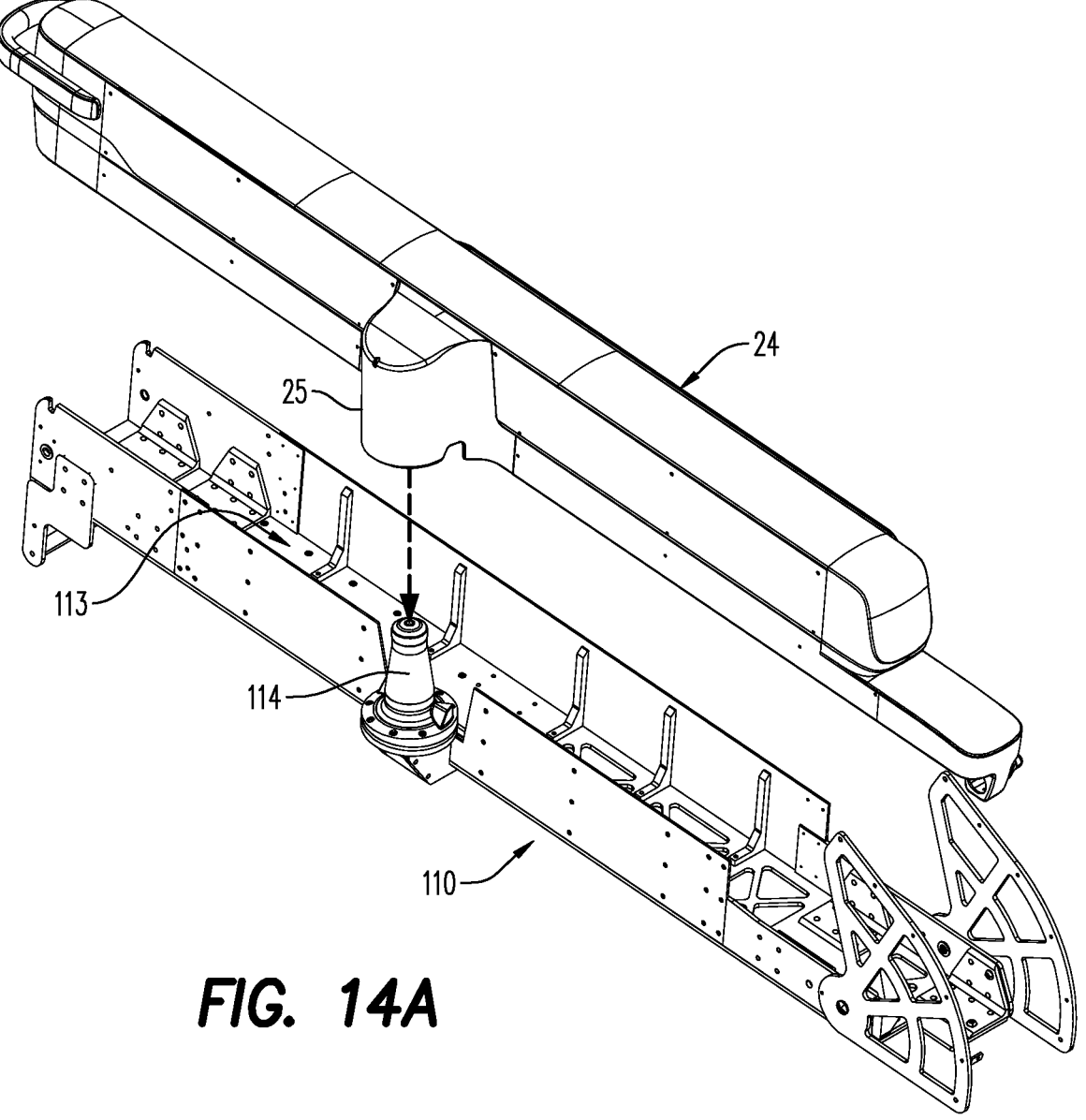
FIG. 14A is a top perspective view illustrating placement of a robotic drive in a tray in accordance with some embodiments.
Figure 14B:
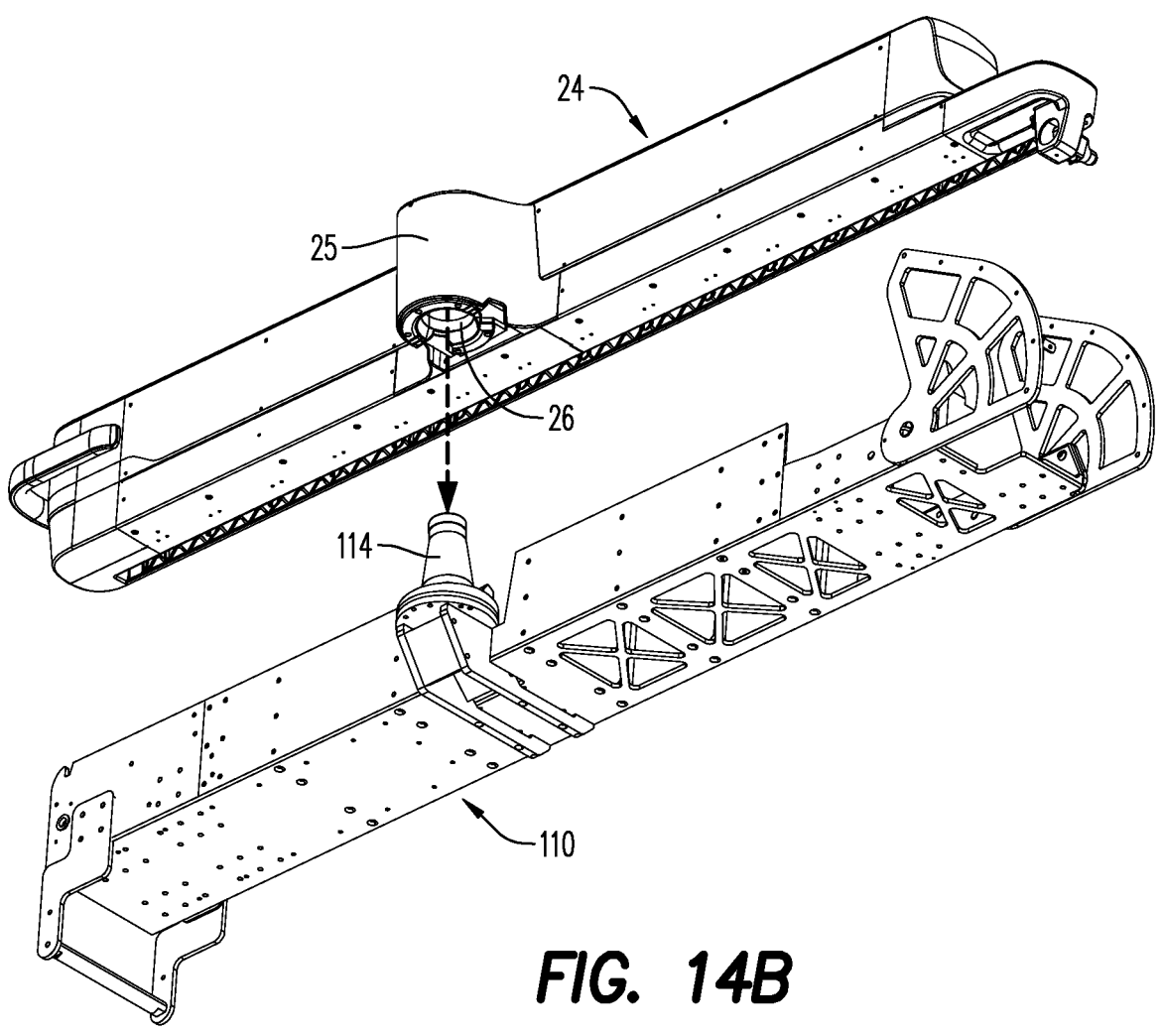
FIG. 14B is a bottom perspective view illustrating placement of a robotic drive in a tray in accordance with some embodiments.

FIG. 14A and FIG. 14B are views illustrating placement of robotic drive 24 in tray 110 in accordance with some embodiments. As shown, tray 110 is configured to snugly accept robotic drive 24. Placement of robotic drive 24 includes aligning robotic drive 24 with internal volume 113 and projection interface 114 with receptacle 26 defined by housing 25 of robotic drive 24. Once aligned, robotic drive 24 is lowered into volume 113 such that projection interface 114 is accepted into receptacle 26. Tray 110 may include any suitable elements to align and/or secure drive 24. As mentioned above, robotic drive 24 may be completely supported by projection interface 114 such that robotic drive 24 does not touch other surfaces of tray 110 when disposed therein.

Figure 15:
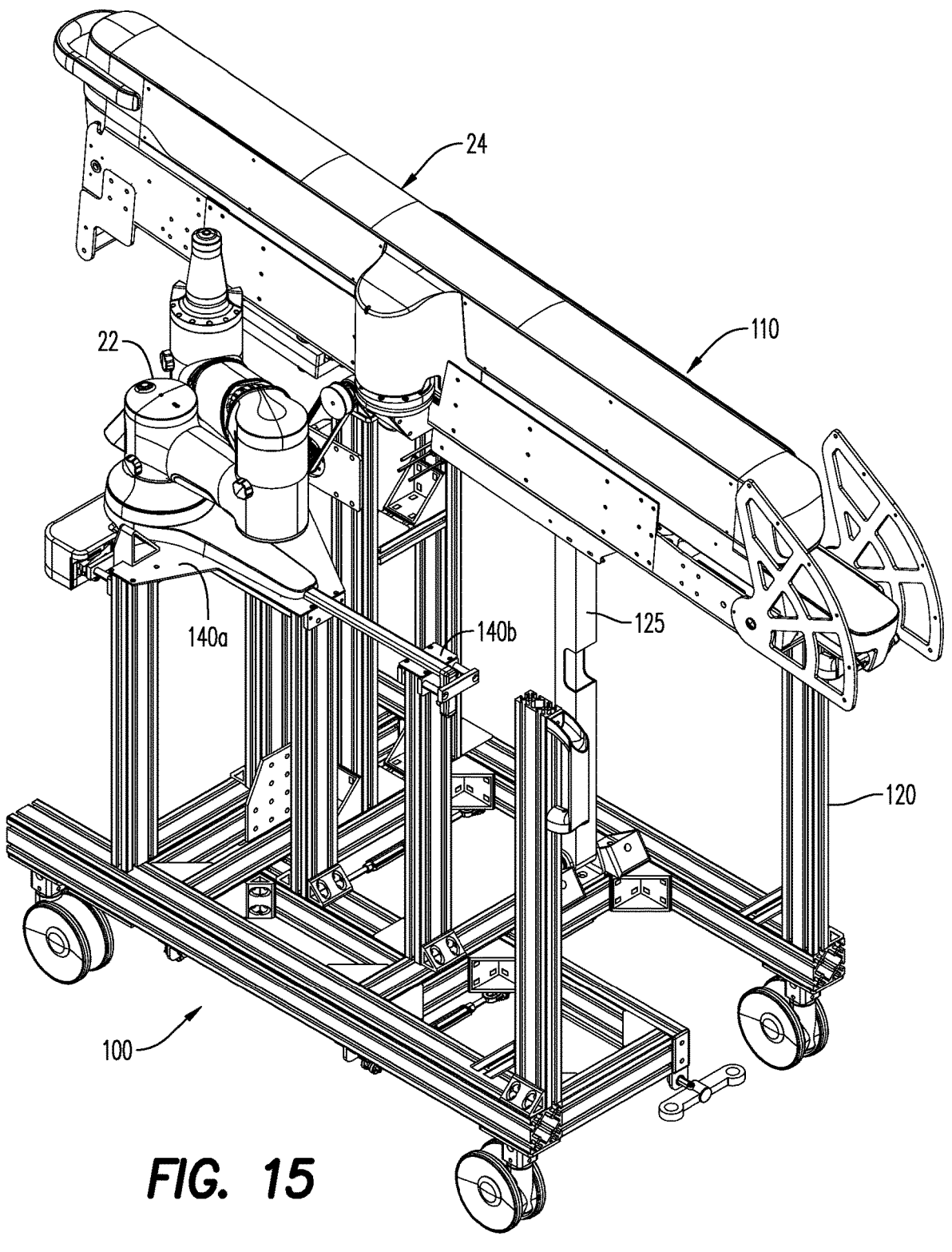
FIG. 15 is a perspective view of a mobile system supporting a robotic drive in a first position in accordance with some embodiments.
Figure 16:
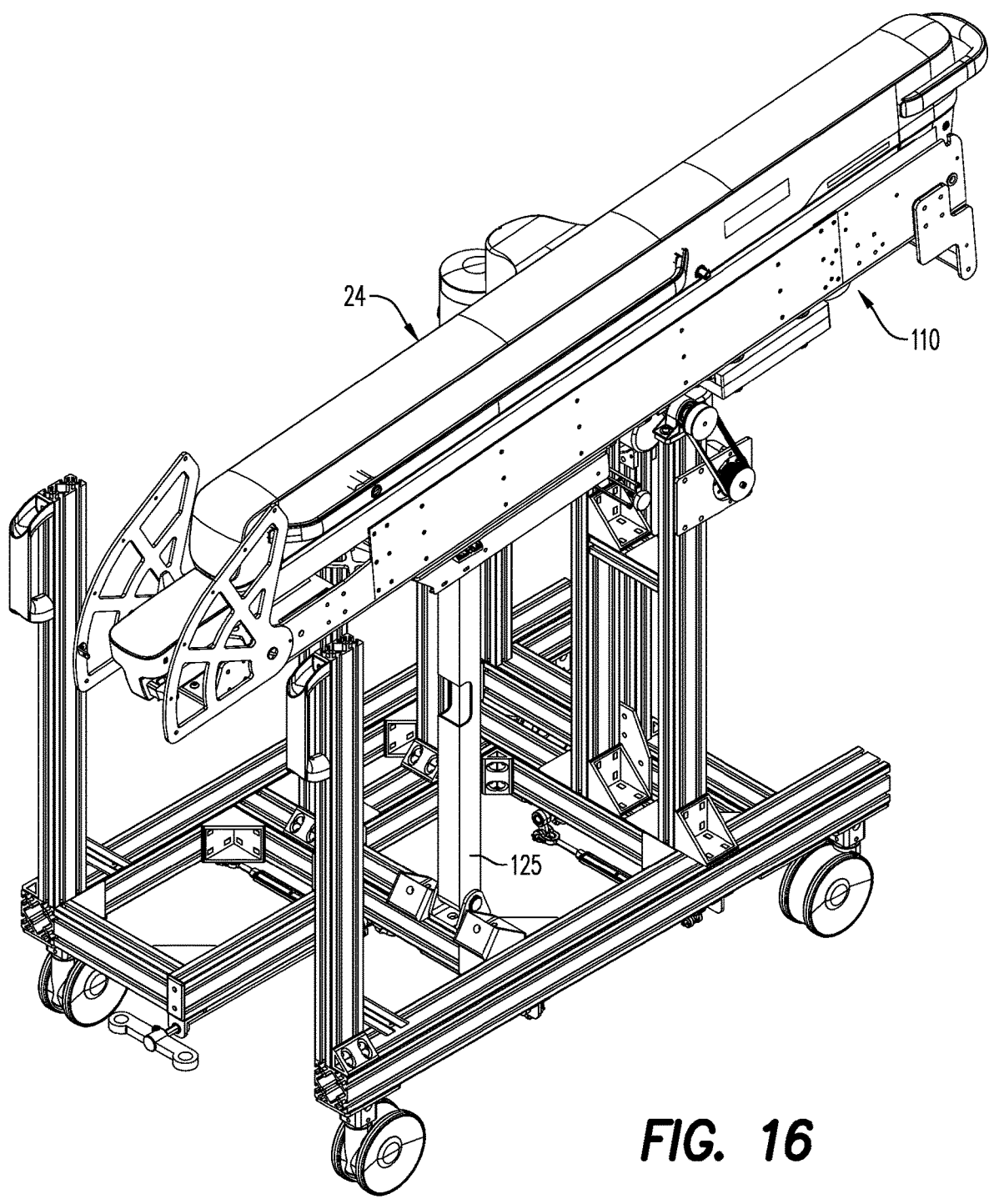
FIG. 16 is a perspective view of a mobile system supporting a robotic drive in a first position in accordance with some embodiments.

FIGS. 15 and 16 show mobile system 100 supporting robotic drive 24 in a substantially horizontal position in accordance with some embodiments. In particular, support arm 125 of cart 120 supports tray 110 in the substantially horizontal position, which in turn supports robotic drive 24. As also shown, positioning device 22 is mounted on platforms 140a and 140b of cart 120.

According to some embodiments, mobile system 100 is moved to a patient support to which positioning system 22 is attached. Casters 135a-135c are then locked to stabilize system 100. Robotic drive 24 is detached from positioning system 22 and placed in tray 110, followed by placement of positioning system 22 on platforms 140a and 140b, resulting in the configuration shown in FIGS. 15 and 16.

Figure 17:
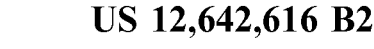
FIG. 17 is a perspective view of a mobile system supporting a robotic drive in a second position in accordance with some embodiments.
Figure 18:
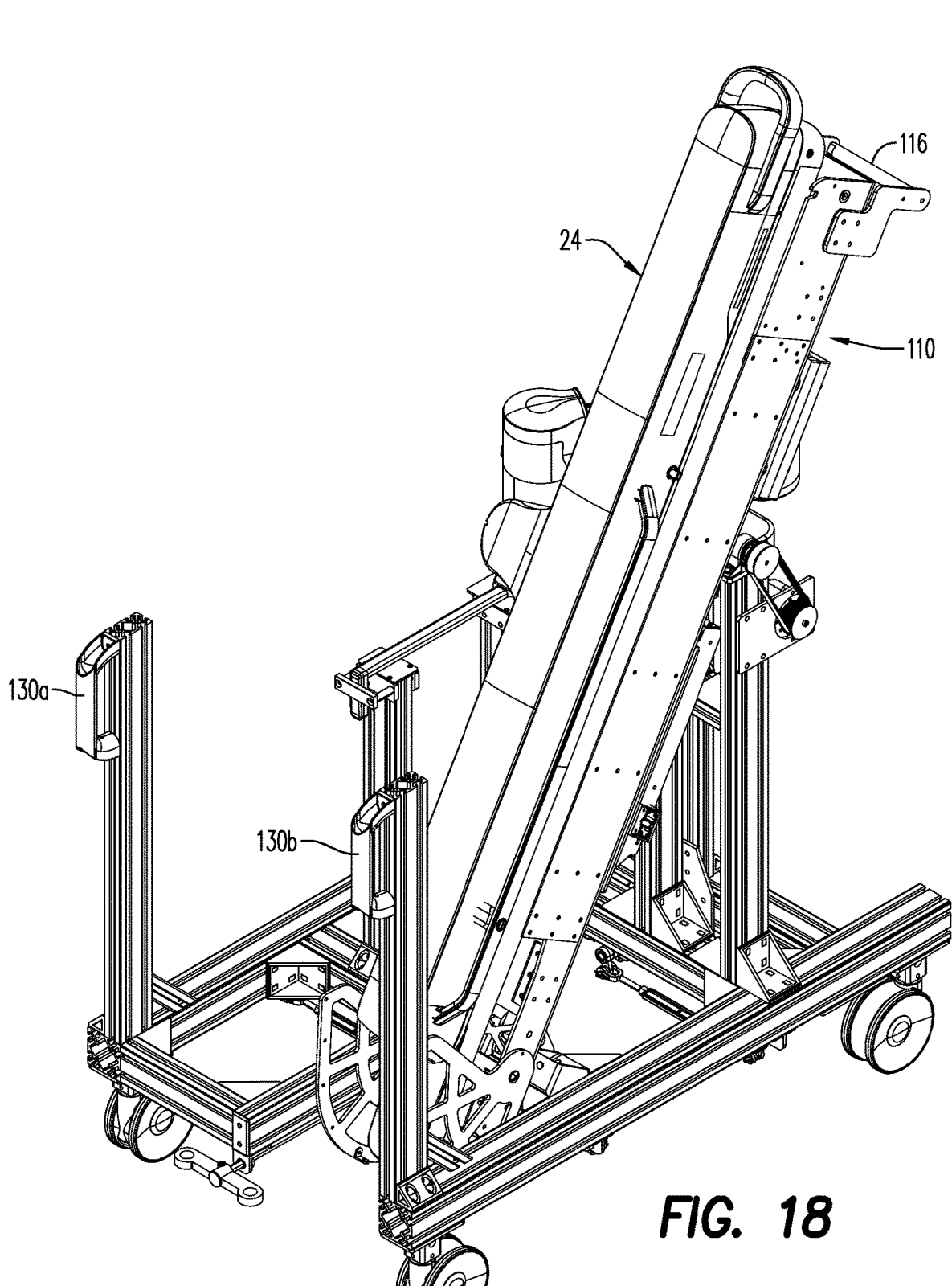
FIG. 18 is a perspective view of a mobile system supporting a robotic drive in a second position in accordance with some embodiments.

FIGS. 17 and 18 show mobile system 100 supporting robotic drive 24 in a position which may be used to transport and store robotic drive 24 in some embodiments. As will be described in detail below, support arm 125 of cart 120 has been unlocked to allow rotation of tray 110 to the position shown in FIGS. 17 and 18.

Once in the illustrated position, an operator may unlock casters 135a-135c and use handles 130a and 130b to transport system 100 and robotic drive 24 to a next catheter-based procedure or to a storage area. Once transport system 100 and robotic drive 24 arrive at a next procedure, an operator may lock casters 135a-135c, detach positioning system 22, and attach positioning system 22 to a patient support. Next, the operator may use handle 116 to rotate tray 110 (and robotic drive 24) to the position shown in FIGS. 15 and 16 until support arm locks in place (as described below), remove robotic drive 24 from tray 110, and attach robotic drive 24 to positioning system 22.

Figure 19:
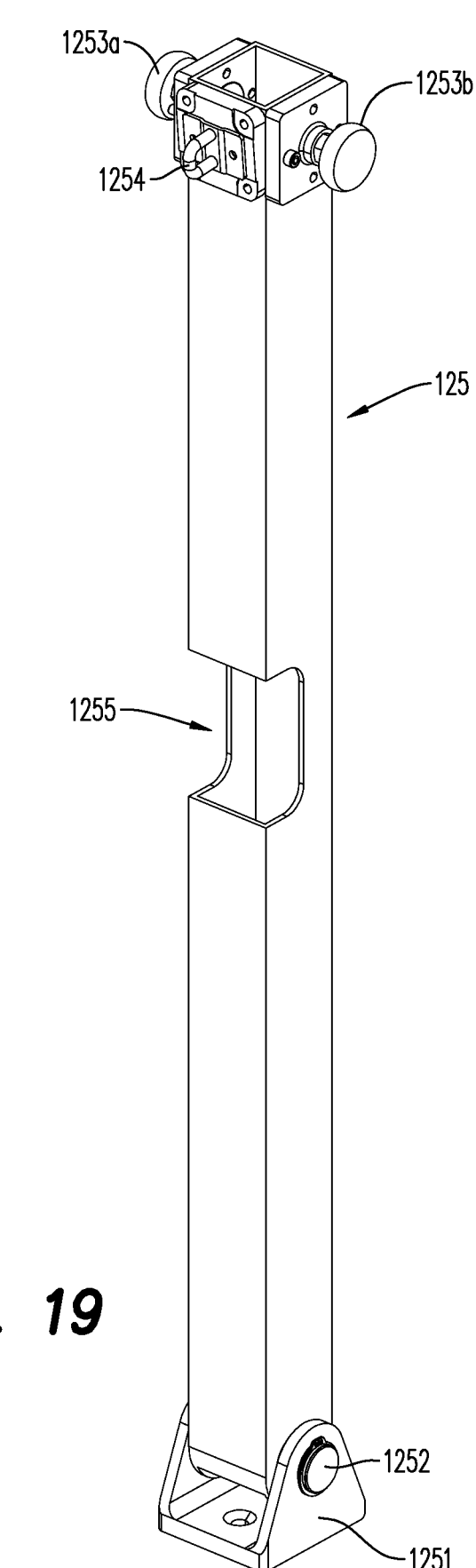
FIG. 19 is a perspective view of a support arm of a mobile system in accordance with some embodiments.

FIG. 19 is a perspective view of support arm 125 of a mobile system 100 in accordance with some embodiments. Support arm 125 is rotatably coupled to horizontal member 126 of cart 120 via bracket 1251 such that support arm 125 may pivot around pin 1252. Also coupled to support arm 125 are track rollers 1253a and 1253b, which movably couple an end of support arm 125 to tray 110 as will be described below.

Strikeplate 1254 is coupled to support arm 125. While support arm 125 is supporting tray 110 in the above-mentioned substantially horizontal position, strikeplate 1254 engages with a locking mechanism to prevent movement of support arm 125. Accordingly, while strikeplate 1254 engages with the locking mechanism, tray 110 is prevented from rotating toward the transport and storage position.

Figure 20:
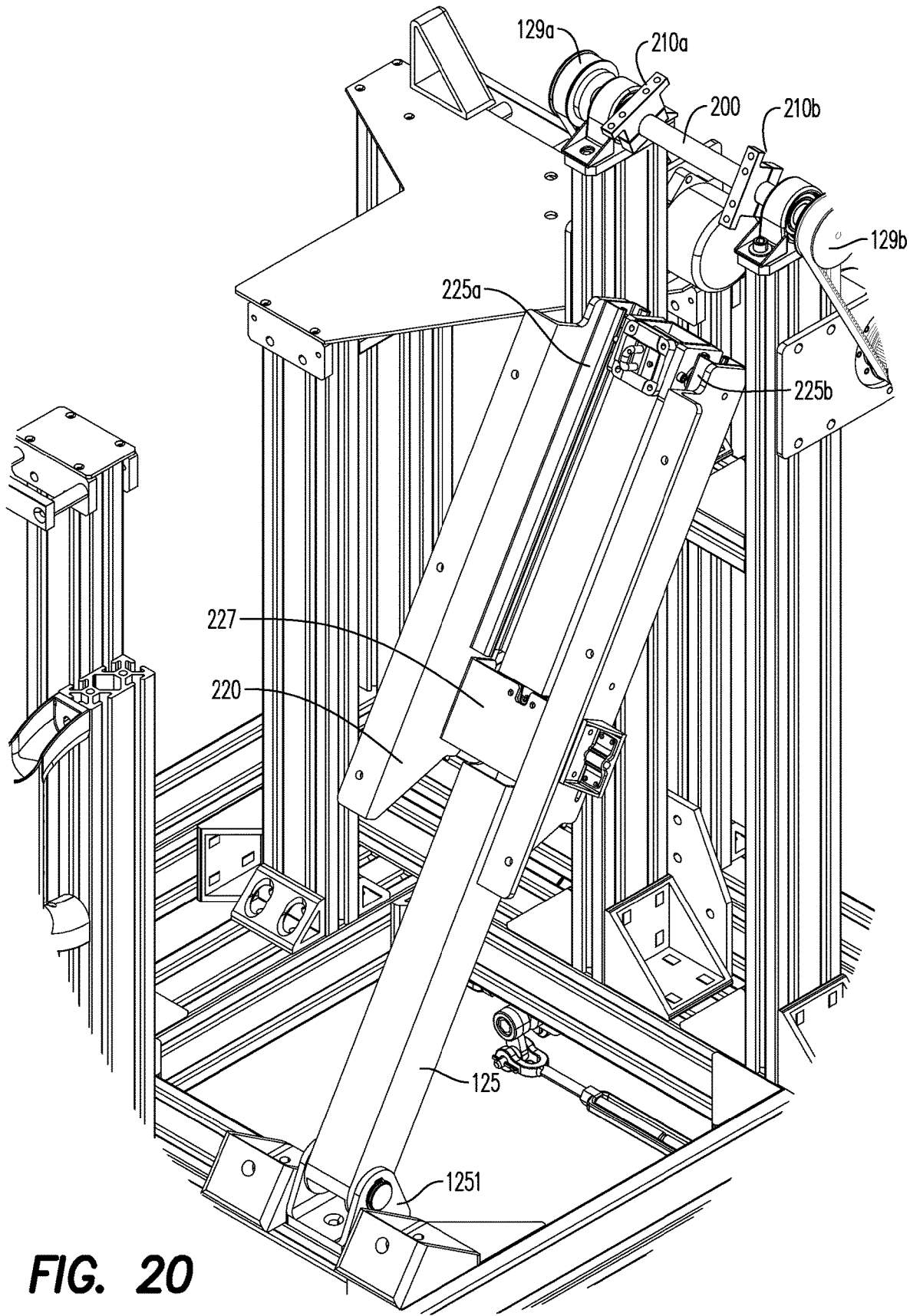
FIG. 20 is a perspective view of a portion of a mobile system to illustrate a support arm positioned prior to movement of a tray to a substantially horizontal position from a second position which is less horizontal than the substantially horizontal position in accordance with some embodiments.
Figure 21:
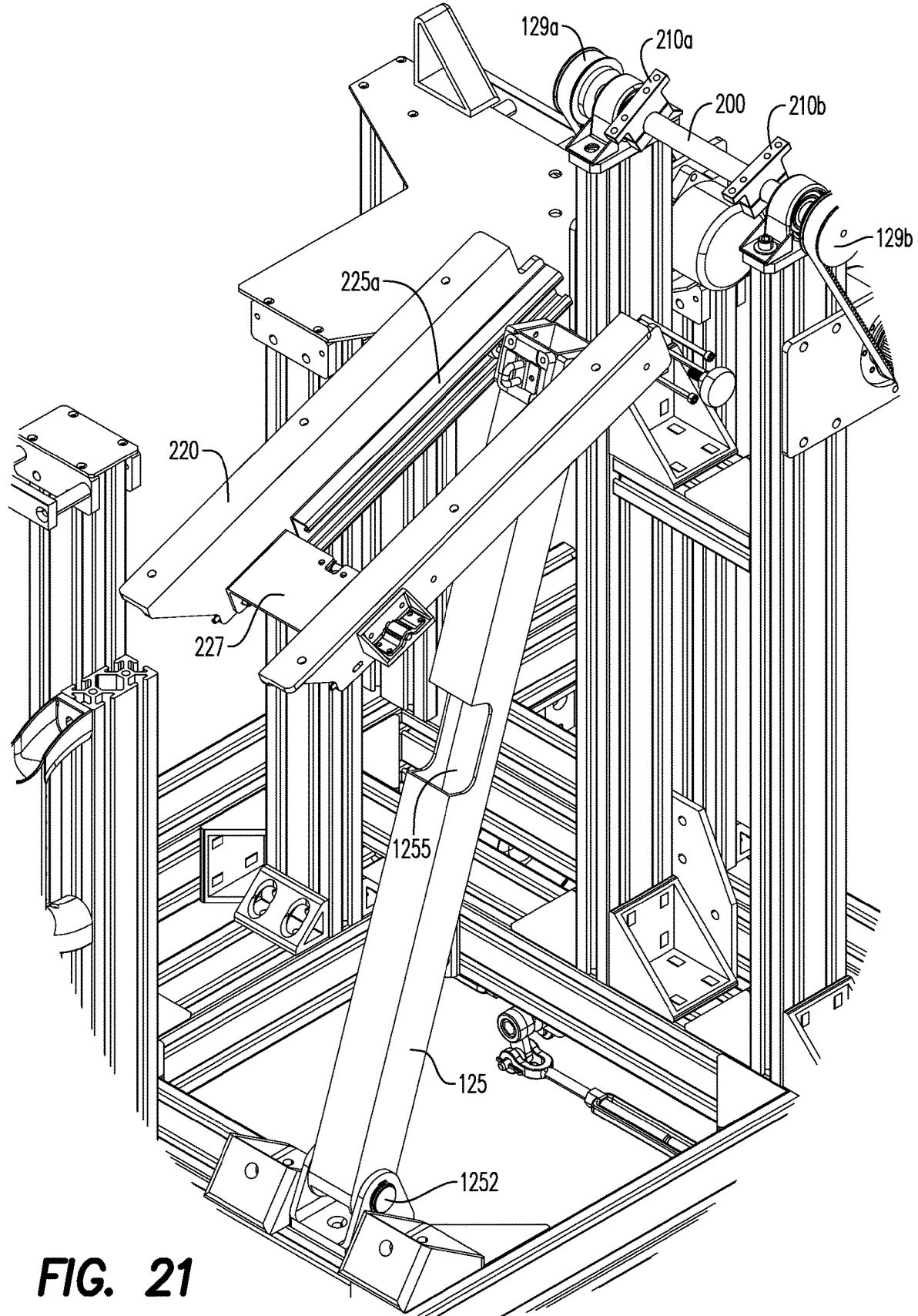
FIG. 21 is a perspective view of a portion of a mobile system to illustrate movable coupling of a support arm to a tray during movement of the tray to a substantially horizontal position from a second position which is less horizontal than the substantially horizontal position in accordance with some embodiments.
Figure 22:
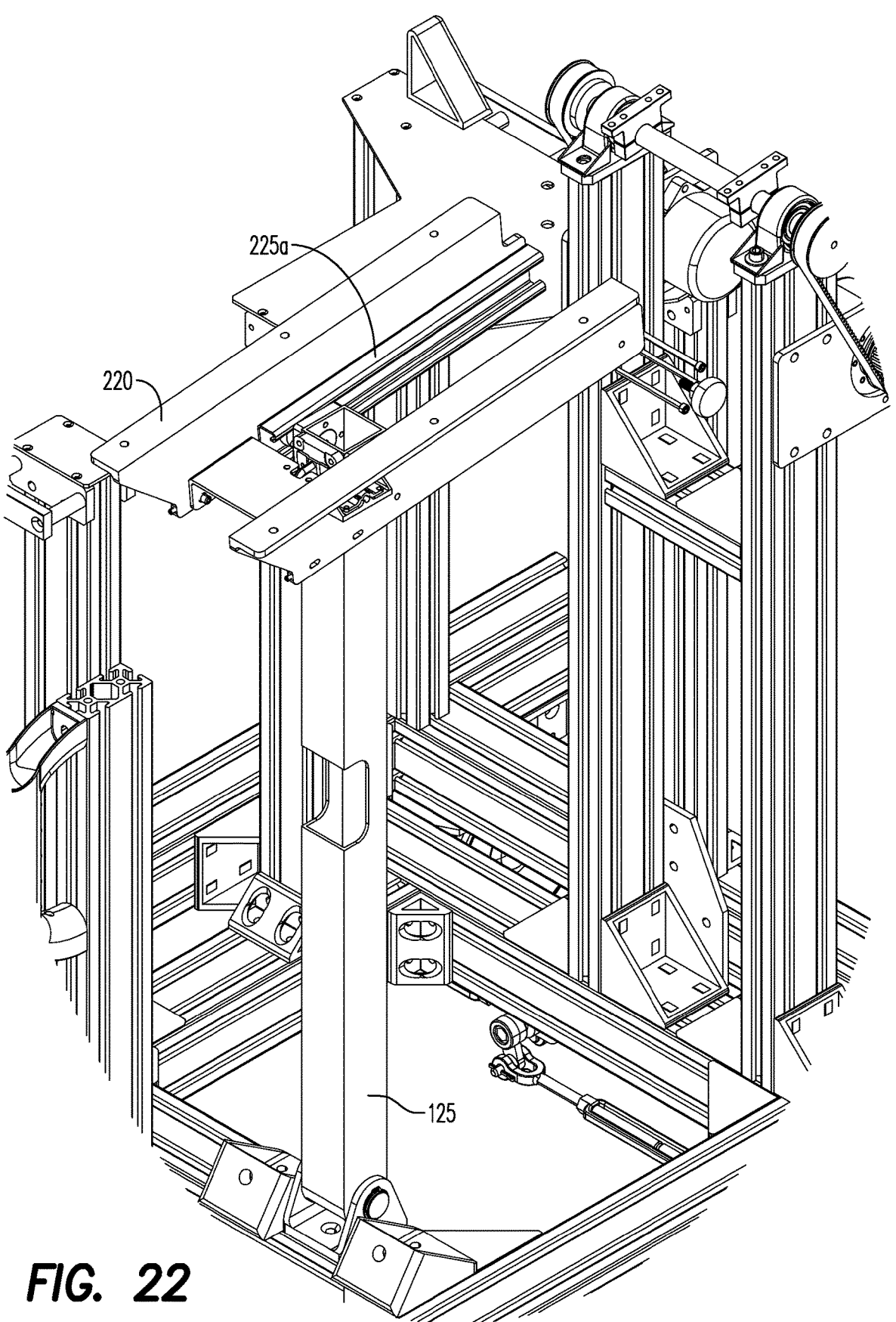
FIG. 22 is a perspective view of a portion of a mobile system including a support arm positioned to support a tray in a substantially horizontal position in accordance with some embodiments.

FIGS. 20-22 are perspective views to illustrate movement of support arm 125 during rotation of tray 110 according to some embodiments. For clarity, tray 110 is omitted from FIGS. 20-22. It will be assumed that tray portion 220 is secured to tray 110.

In FIG. 20, support arm 125 is collapsed and tray 110 is assumed to be in the transport and storage position. Axle 200 is fixedly coupled to tray 110 via mounts 210a and 210b. Accordingly, rotation of tray 110 results in corresponding rotation of axle 200.

Tray portion 220 defines roller tracks 225a and 225b in which rollers 1253a and 1253b are disposed. Tray portion 220 also includes brace 227 to provide rigidity to tray portion 220. Brace 227 resides in notch 1255 of support arm 125 while in the FIG. 20 position.

FIG. 21 represents rotation of tray 110 about axle 200. For example, an operator has pulled downward on handles 116 to begin rotation of tray 110 from the transport and storage position to the substantially horizontal position. Rotation of tray 110 in this direction causes support arm 125 to rotate upward as shown, pivoting about pin 1252. During this rotation, rollers 1253a and 1253b roll in roller tracks 225a and 225b toward brace 227. Moreover, rotation of axle 200 results in rotation of pulleys 128a and 128b, which may be resisted by dampers 127a and/or 127b as described above. FIG. 22 represents a final substantially horizontal position of tray 110. Support arm 125 is fully upright and rollers 1253a and 1253b have reached the end of their travel within roller tracks 225a and 225b.

Figure 23:
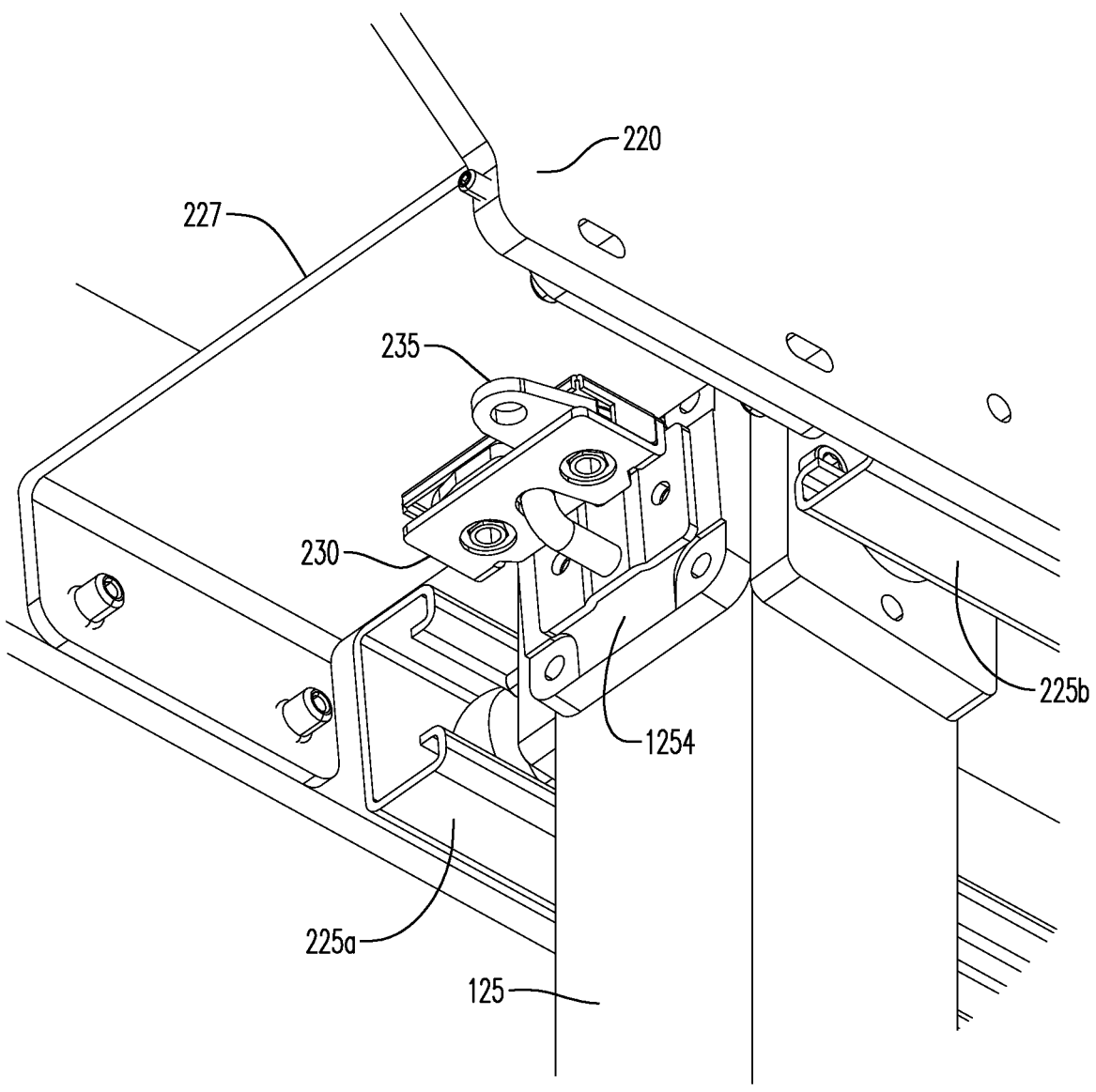
FIG. 23 is a perspective view of a locking mechanism to releasably couple a support arm to a tray when the tray is in a substantially horizontal position in accordance with some embodiments.

FIG. 23 is a close-up perspective view of strikeplate 1254 when support arm 125 is disposed in the position depicted in FIG. 22. In this position, strikeplate 1254 engages with locking mechanism 230 coupled to brace 227 of tray portion 220. Accordingly, support arm 125 remains upright and securely supports tray 110 in the substantially horizontal position. Support arm 125 supports tray 110 at a point spaced substantially from the rotation axis of axle 200, thereby providing stability to tray 110 to improve usability while loading and unloading robotic drive 24.

Locking mechanism 230 and strikeplate 1254 may releasably couple support arm 125 to tray 110 when tray 110 is in a substantially horizontal position. For example, a cable or other device may be attached to pull 235 of locking mechanism 230. Pulling the cable causes locking mechanism 230 to release strikeplate 1254 and allow tray 110 and arm 125 to reverse the movement depicted in FIGS. 20-22.

The cable or other lock-releasing device can easily be located at an arbitrary distance and orientation in relation to mechanism 230, and may be coupled to a cable pull handle. In some embodiments, such a handle is ergonomically designed and integrated into handle 116 such that is easy for an operator to release strikeplate 1254 and pivot tray 110 up or down from a mechanically advantageous position.

The patentable scope of the embodiments described herein is defined by the claims, and may include other examples that occur to those in the art. Such other examples are intended to be within the scope of the claims if they include structural elements that do not differ from the literal language of the claims, or if they include equivalent structural elements with insubstantial differences from the literal language of the claims. The order and sequence of any process or method steps may be varied or re-sequenced according to alternative embodiments.

What is claimed is:

1. A mobile system for a robotic drive, the mobile system comprising:
    a tray configured to support the robotic drive;
    a cart coupled to the tray;
    one or more wheels coupled to the cart;
    an axle fixedly coupled to the tray;
    a column fixedly coupled to the cart in a substantially vertical position and to support the axle;
    a support arm coupled to the cart and configured to support the tray in a substantially horizontal position, a first end of the support arm movably coupled to the tray and a second end of the support arm rotatably coupled to the cart, the support arm configured to, during pivoting of the tray around the axle to move the tray from the substantially horizontal position to a second position, pivot around the second end while the first end moves along the tray toward the axle; and
    an assembly coupled to the cart and configured to resist pivoting of the tray from the substantially horizontal position to the second position.

2. A mobile system according to claim 1, wherein the assembly comprises:
    a mechanism configured to resist rotation of the axle during the pivoting of the tray from the substantially horizontal position to the second position.

3. A mobile system according to claim 2, wherein the mechanism transfers torque to the axle during the pivoting of the tray from the substantially horizontal position to the second position.

4. A mobile system according to claim 2, wherein the assembly is configured to allow pivoting from the second position to the substantially horizontal position, and
    wherein the mechanism does not substantially resist rotation of the axle during the pivoting of the tray from the second position to the substantially horizontal position.

5. A mobile system according to claim 1, the cart comprising a locking mechanism configured to releasably couple the support arm to the tray when the tray is in the substantially horizontal position.

6. A mobile system according to claim 1, wherein the tray comprises a base and two opposing side walls, and wherein at least one of the opposing side walls is movable with respect to the base.

7. A mobile system for a robotic drive, the mobile system comprising:
    a tray configured to support the robotic drive;
    an axle fixedly coupled to the tray;
    a cart comprising:
    a column fixedly coupled to the cant in a substantially vertical position and to support the axle;
    a support arm configured to support the tray in a substantially horizontal position, a first end of the support arm movably coupled to the tray and a second end of the support arm rotatably coupled to the cart, the support arm configured to, during pivoting of the tray around the axle to move the tray from the substantially horizontal position to a second position, pivot around the second end while the first end moves along the tray toward the axle; and
    one or more wheels coupled to the cart.

8. A mobile system according to claim 7, the cart comprising a locking mechanism configured to releasably couple the support arm to the tray when the tray is in the substantially horizontal position.

9. A mobile system according to claim 7, the cart comprising:
    a mechanism to resist rotation of the axle during the pivoting of the tray from the substantially horizontal position to the second position.

10. A mobile system according to claim 9, wherein the mechanism transfers torque to the axle during the pivoting of the tray from the substantially horizontal position to the second position and does not substantially resist rotation of the axle during the pivoting of the tray from the second position to the substantially horizontal position.

11. A mobile system according to claim 7, wherein the tray comprises a base and two opposing side walls, and wherein at least one of the opposing side walls is movable with respect to the base.

12. A method for operating a mobile system for a robotic drive, the method comprising:
    placing the robotic drive into a tray of the mobile system, the tray configured to support the robotic drive;
    unlocking a locking mechanism fixedly coupling a support arm to the tray while the support arm and a column fixedly coupled to the mobile system support the tray in a substantially horizontal position, where a first end of the support arm is movably coupled to the tray and a second end of the support arm is rotatably coupled to the mobile system; and
    pivoting the tray around an axle fixedly coupled to the tray and supported by the column to move the tray from the substantially horizontal position to a second position which is less horizontal than the substantially horizontal position,
    wherein, during pivoting of the tray to move the tray from the substantially horizontal position to the second position, the support arm pivots around the second end and the first end moves along the tray toward the axle.

13. A method according to claim 12, wherein pivoting the tray comprises biasing a handle coupled to the tray in a substantially vertical direction.

*    *    *    *    *